(12) United States Patent
Sakai

(10) Patent No.: US 11,760,035 B2
(45) Date of Patent: Sep. 19, 2023

(54) ELASTIC MEMBER AND DISPOSABLE WEARING ARTICLE INCLUDING ELASTIC MEMBER

(71) Applicant: Daio Paper Corporation, Ehime (JP)

(72) Inventor: Syunsuke Sakai, Tochigi (JP)

(73) Assignee: Daio Paper Corporation, Ehime (JP)

( * ) Notice: Subject to any disclaimer, the term of this patent is extended or adjusted under 35 U.S.C. 154(b) by 846 days.

(21) Appl. No.: 16/637,516

(22) PCT Filed: Aug. 24, 2018

(86) PCT No.: PCT/JP2018/031281
§ 371 (c)(1),
(2) Date: Feb. 7, 2020

(87) PCT Pub. No.: WO2019/065024
PCT Pub. Date: Apr. 4, 2019

(65) Prior Publication Data
US 2020/0214363 A1    Jul. 9, 2020

(30) Foreign Application Priority Data

Sep. 27, 2017  (JP) ................................. 2017-187179

(51) Int. Cl.
*A61F 13/49* (2006.01)
*B29C 65/00* (2006.01)
(Continued)

(52) U.S. Cl.
CPC ...... *B29C 66/7294* (2013.01); *A61F 13/4902* (2013.01); *A61F 13/496* (2013.01);
(Continued)

(58) Field of Classification Search
CPC .............. A61F 13/4902; A61F 13/496; A61F 2013/49022; B29L 2031/4878
See application file for complete search history.

(56) References Cited

U.S. PATENT DOCUMENTS

2018/0008481 A1    1/2018 Takahashi et al.
2019/0117469 A1    4/2019 Kunihiro

FOREIGN PATENT DOCUMENTS

| CN | 107205859 | 9/2017 |
| JP | 10-29259 | 6/2000 |

(Continued)

OTHER PUBLICATIONS

International Search Report for PCT/JP2018/031281, dated Sep. 18, 2018.

*Primary Examiner* — Khaled Annis
(74) *Attorney, Agent, or Firm* — ANDRUS INTELLECTUAL PROPERTY LAW, LLP

(57) ABSTRACT

An elastic member which has low stretching stress in a stretchable direction in a stretchable structure of an elastic sheet and is excellent in a feeling of wearing in the case of being applied to an absorbent article. An elastic sheet stretchable structure is provide in which an elastic film is stacked between a first sheet layer having air permeability and a second sheet layer having air permeability, and the first sheet layer and the second sheet layer are bonded through joint holes penetrating the elastic film at a plurality of sheet joined portions arranged at intervals. The joined portions have first joined portions and second joined portions, a plurality of rows of the first joined portions is formed at intervals in a stretchable direction, and rows of the second joined portions having a short length are formed between the rows of the first joined portions.

4 Claims, 27 Drawing Sheets

(51) Int. Cl.
*A61F 13/496* (2006.01)
*B29C 65/08* (2006.01)
*B32B 5/02* (2006.01)
*B32B 7/12* (2006.01)
*B32B 27/12* (2006.01)
*B32B 27/32* (2006.01)
*B29L 31/48* (2006.01)

(52) U.S. Cl.
CPC ............ *B29C 65/086* (2013.01); *B29C 66/21* (2013.01); *B32B 5/022* (2013.01); *B32B 7/12* (2013.01); *B32B 27/12* (2013.01); *B32B 27/32* (2013.01); *A61F 2013/49022* (2013.01); *B29L 2031/4878* (2013.01)

(56) References Cited

FOREIGN PATENT DOCUMENTS

| | | |
|---|---|---|
| JP | 2003-507585 | 2/2003 |
| JP | 2015-204982 | 11/2015 |
| JP | 5967736 | 8/2016 |
| JP | 2017-093732 | 6/2017 |
| JP | 2017-121387 | 7/2017 |
| JP | 2017196296 | 11/2017 |
| WO | 2016-121976 | 8/2016 |
| WO | 2017/086327 | 5/2017 |

[FIG.1]
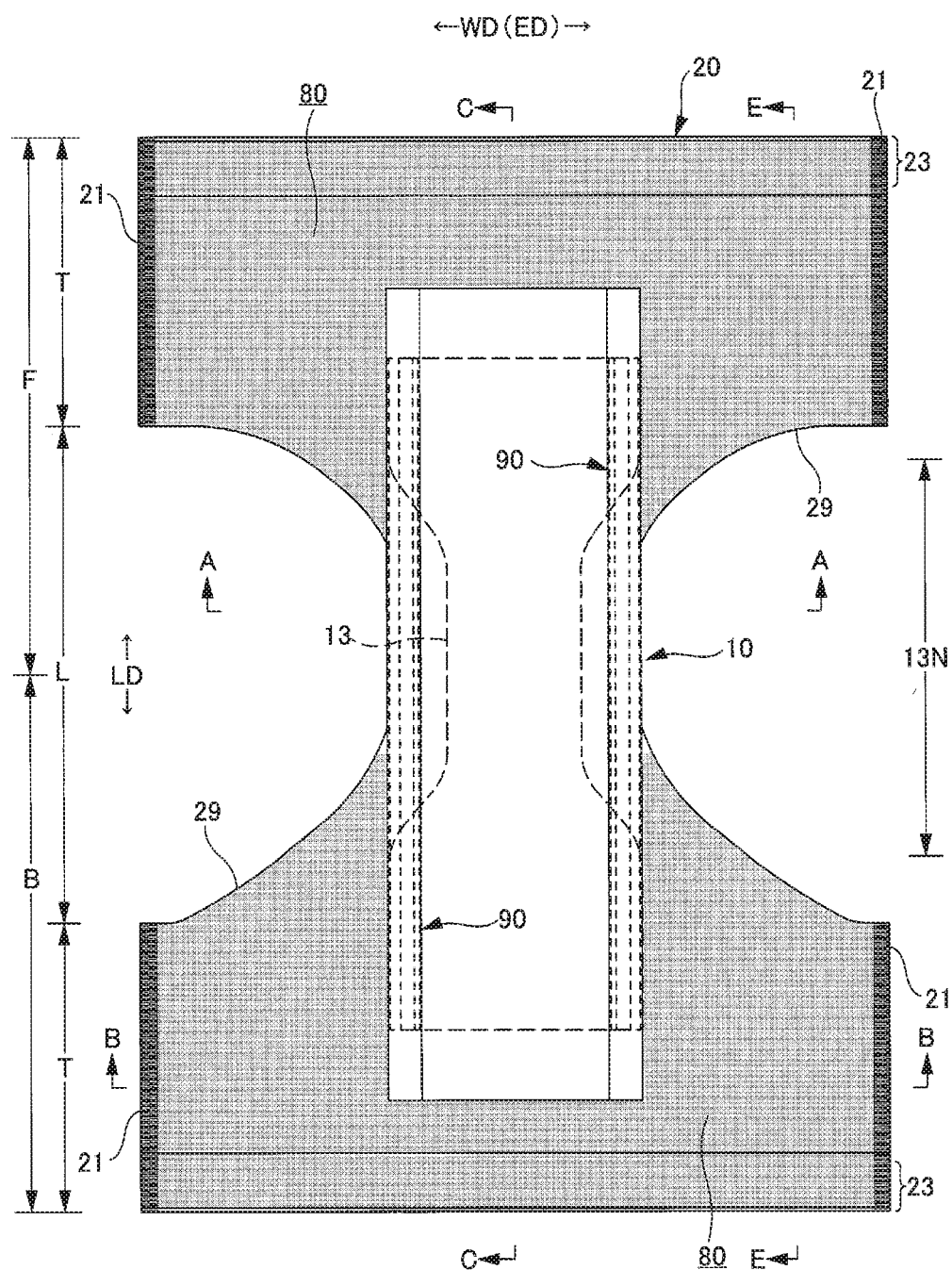

[FIG.2]
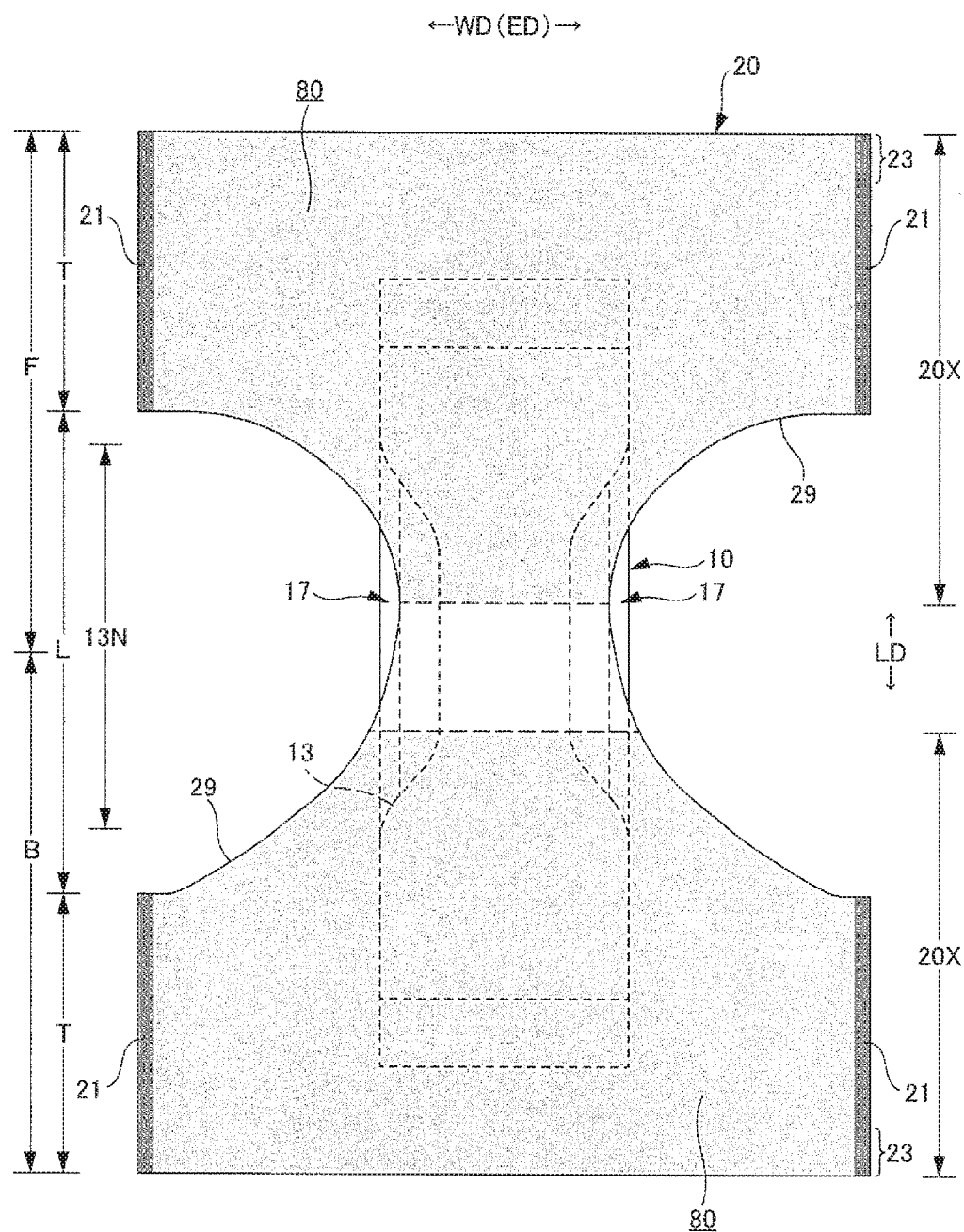

[FIG.3]
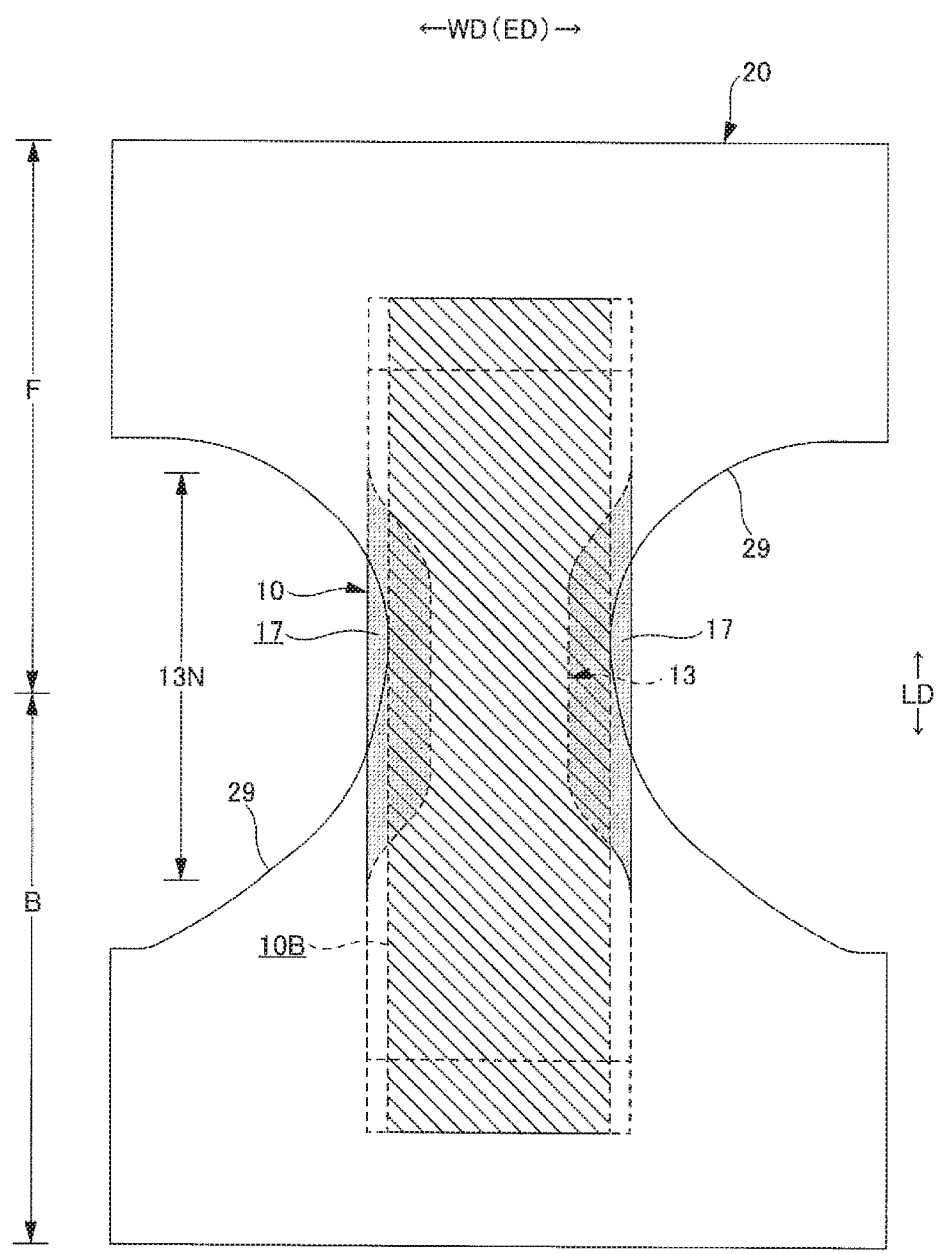

[FIG.4]
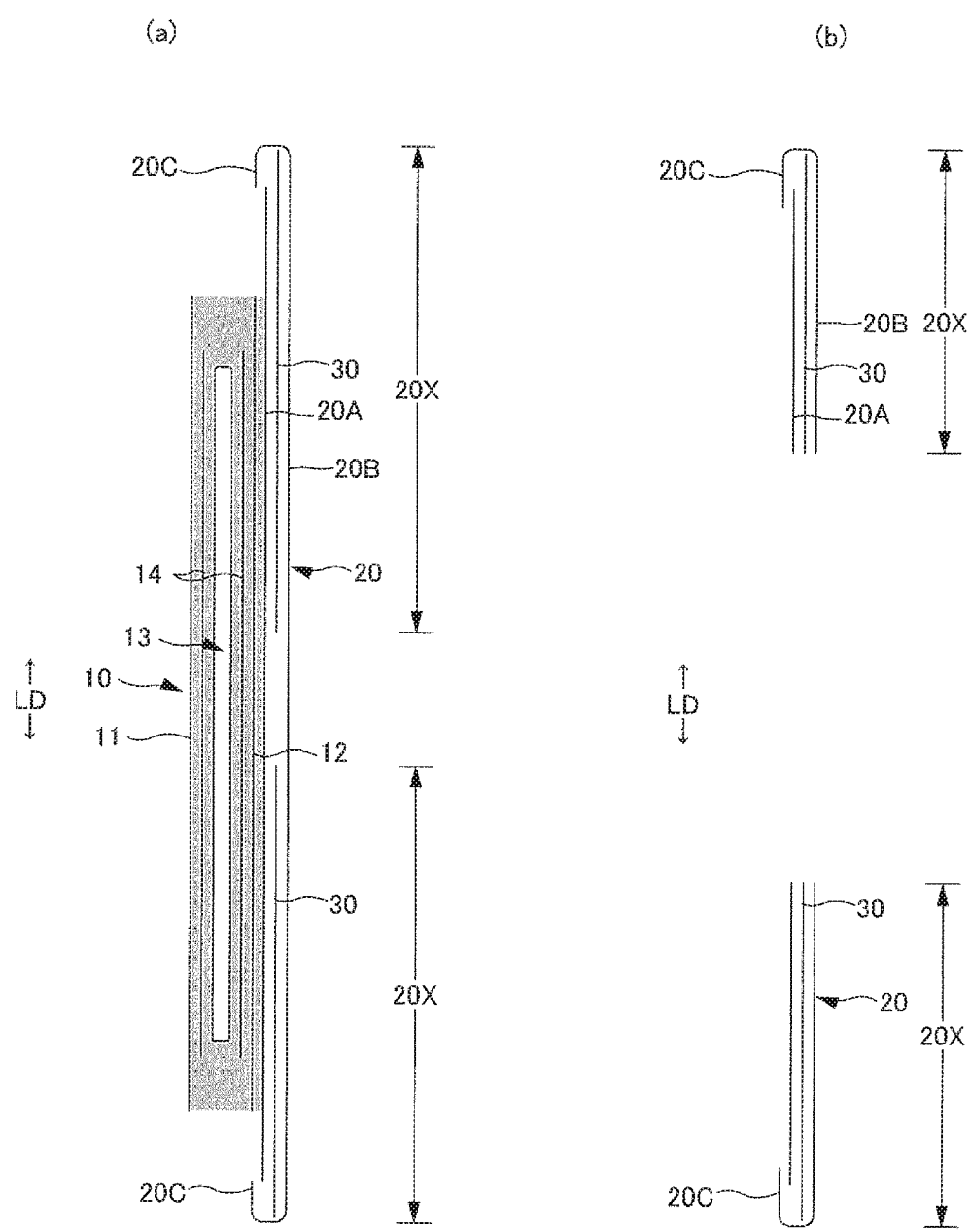

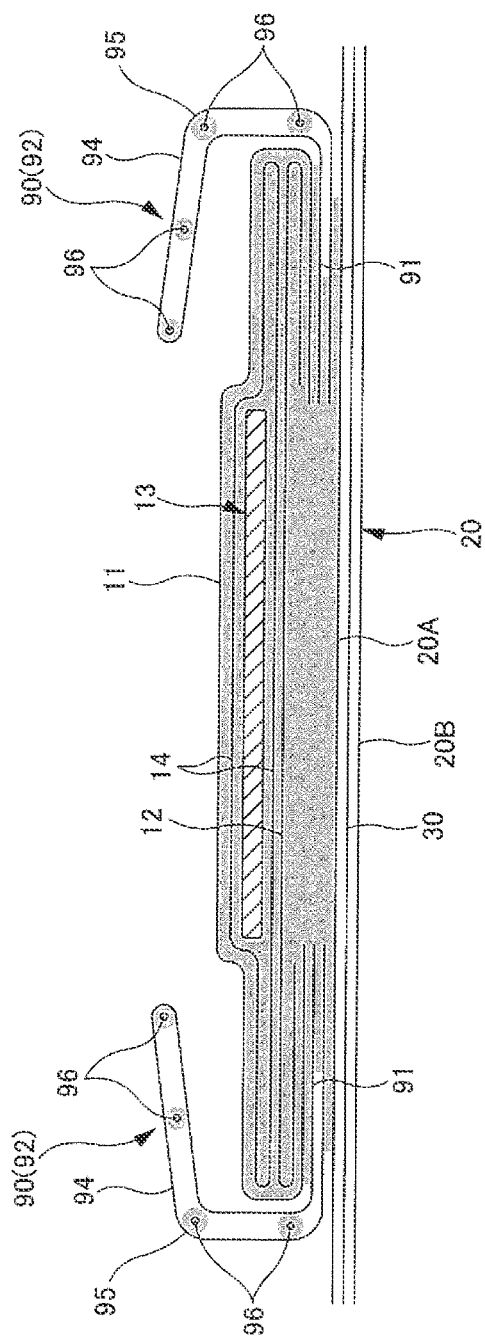

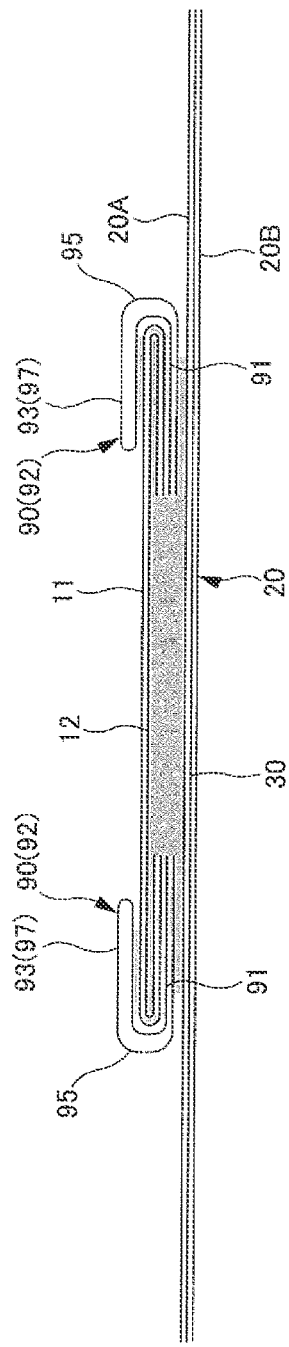

[FIG.7]
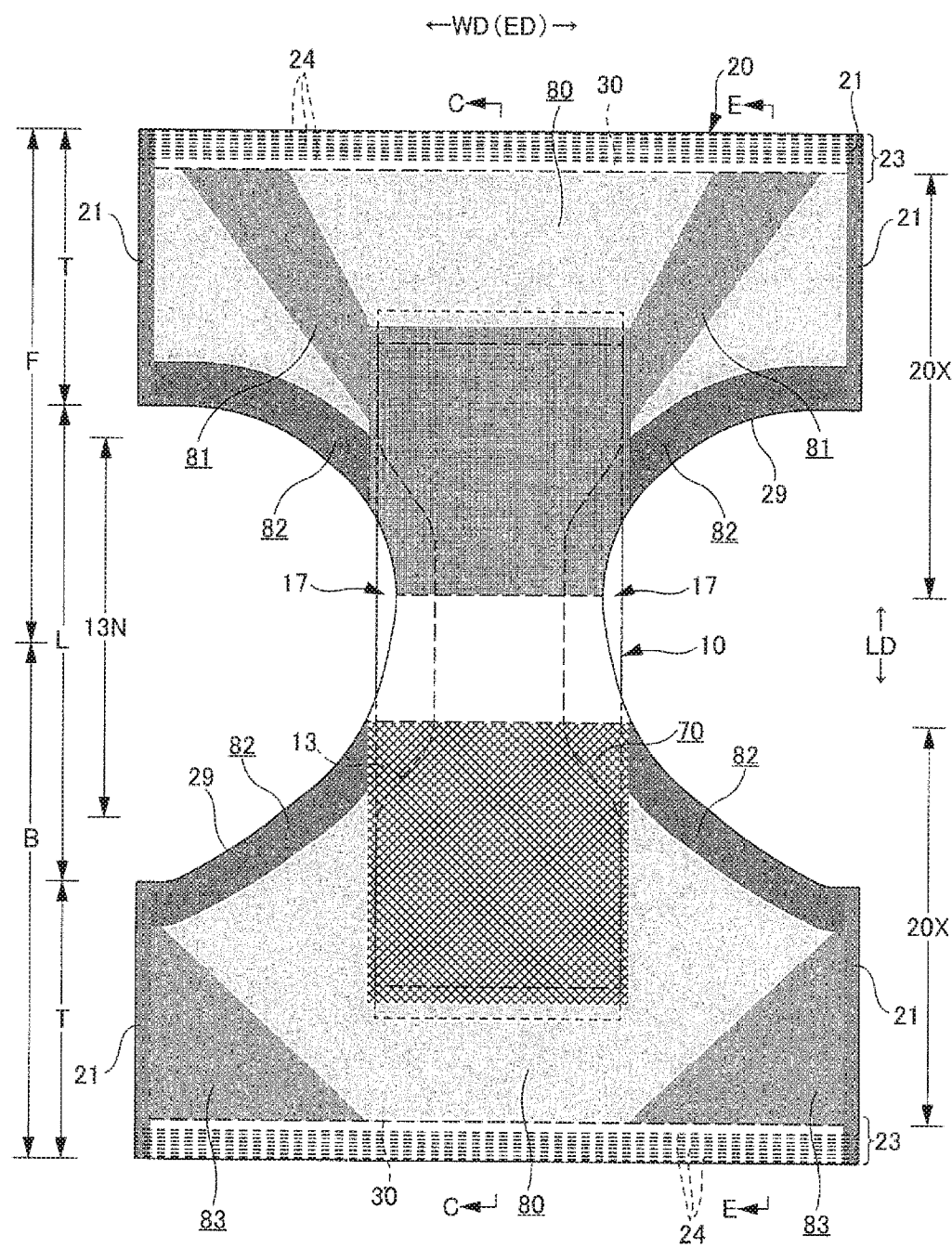

[FIG.8]
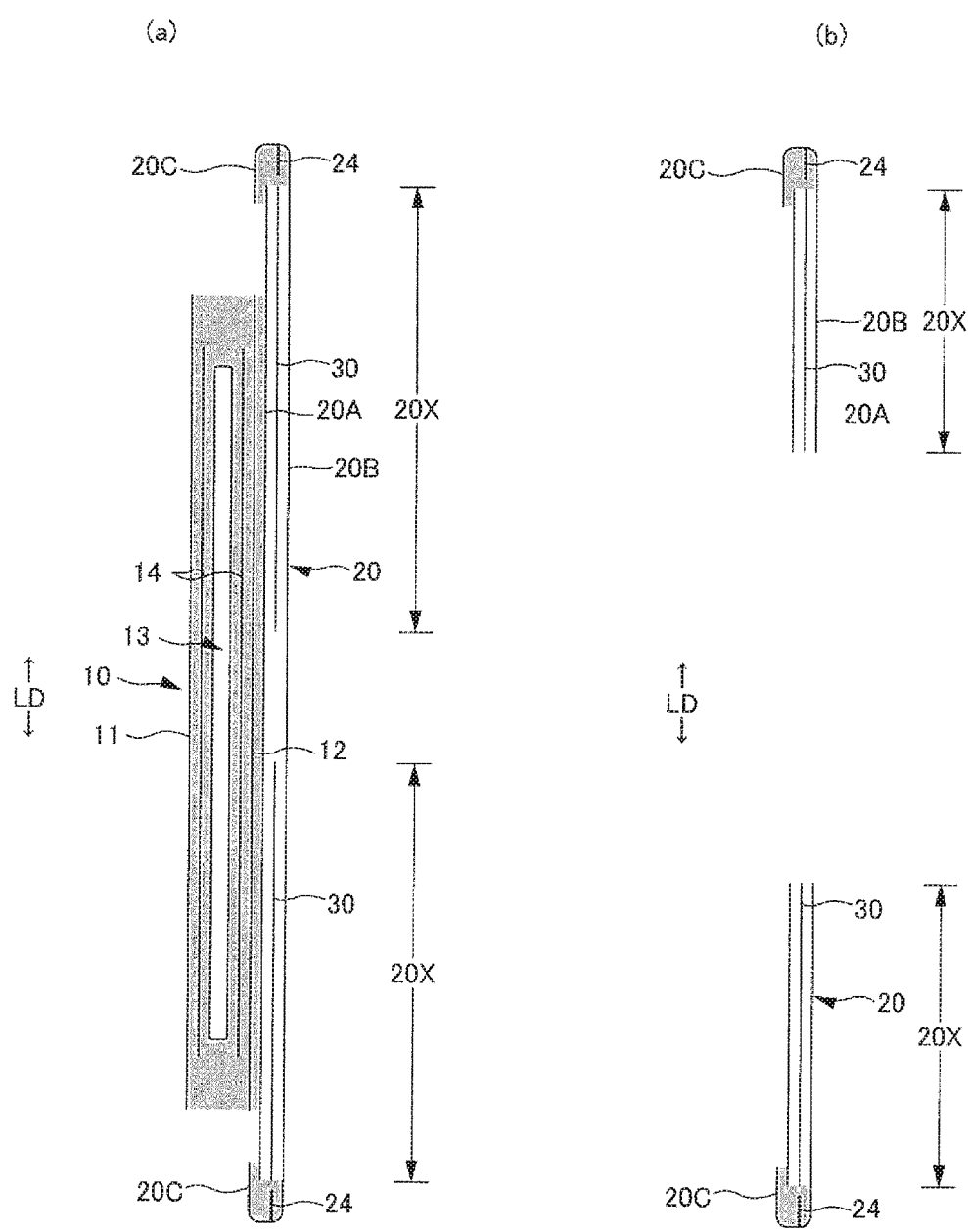

[FIG.9]
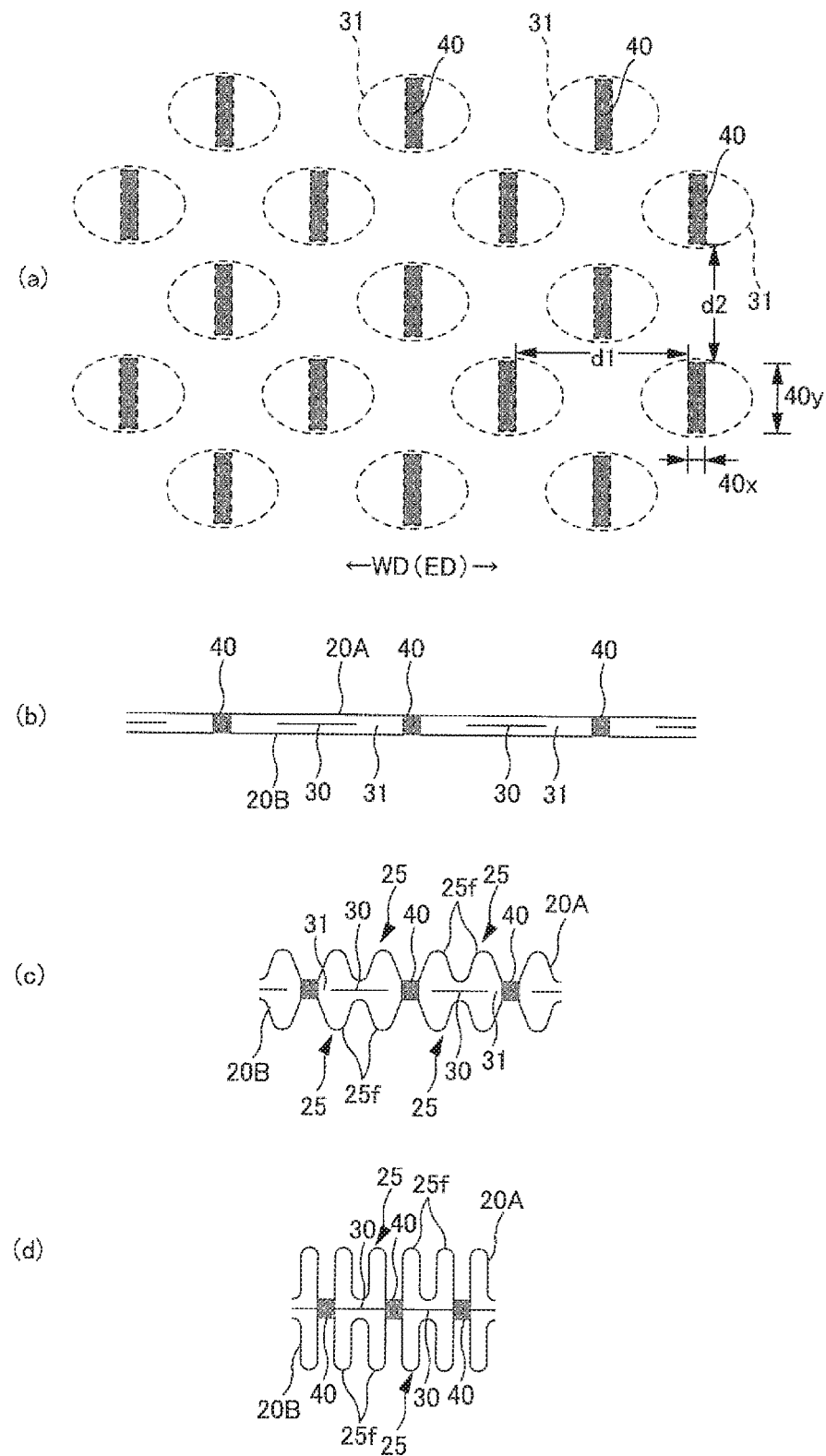

[FIG.10]
(a)
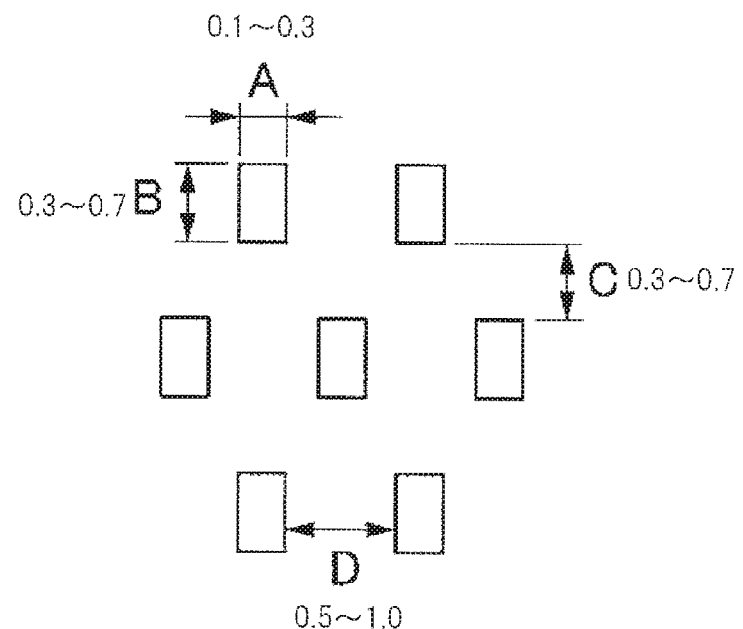
(b)
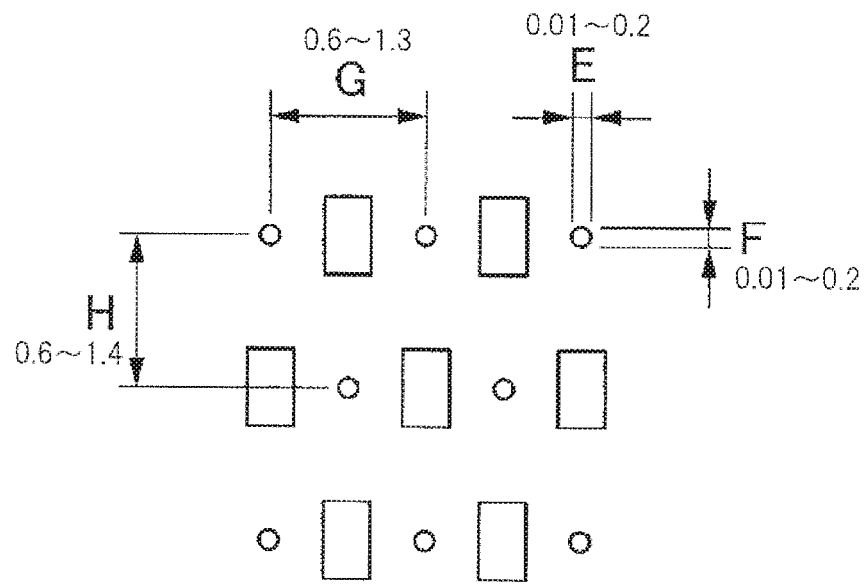

[FIG.11]
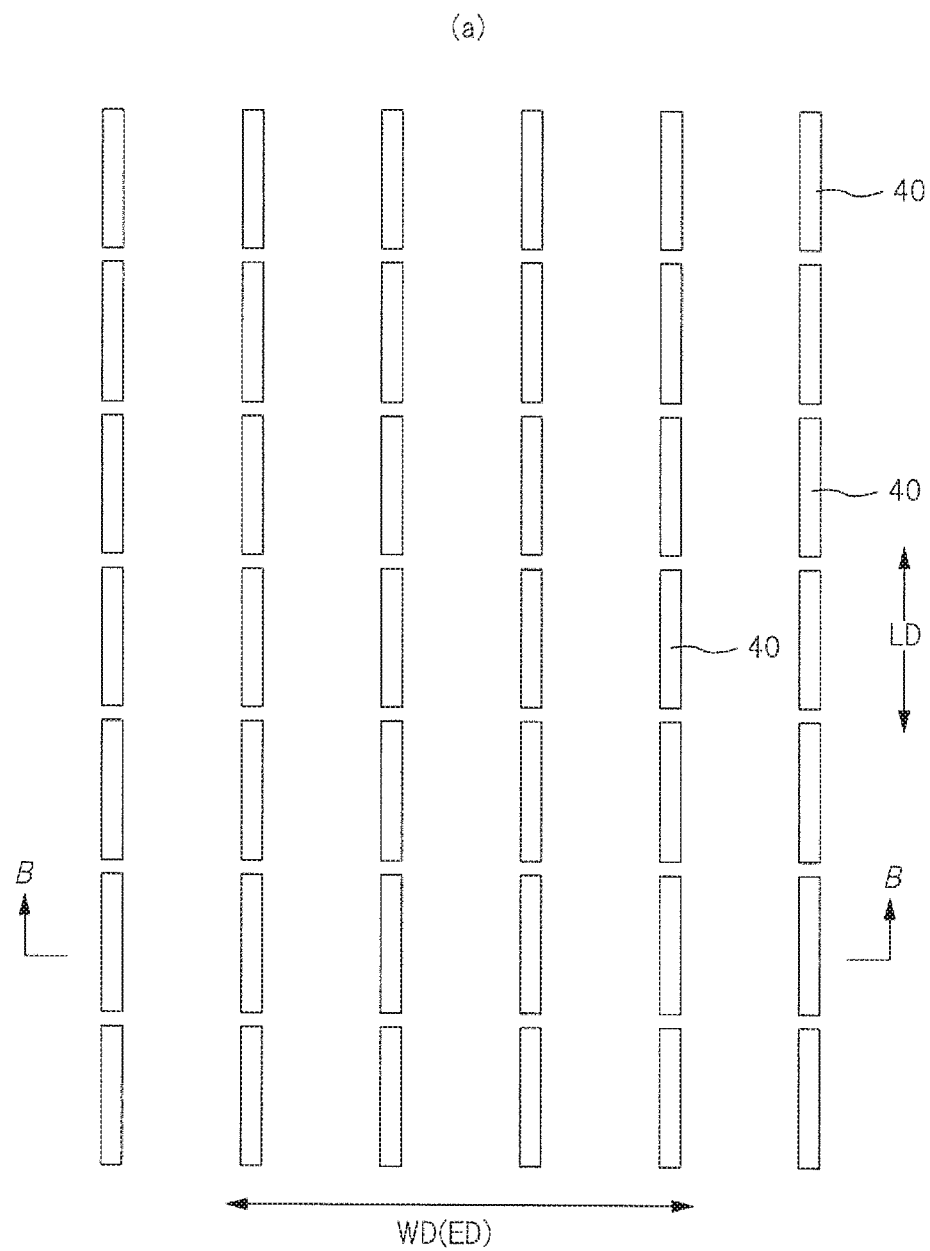

[FIG.12]
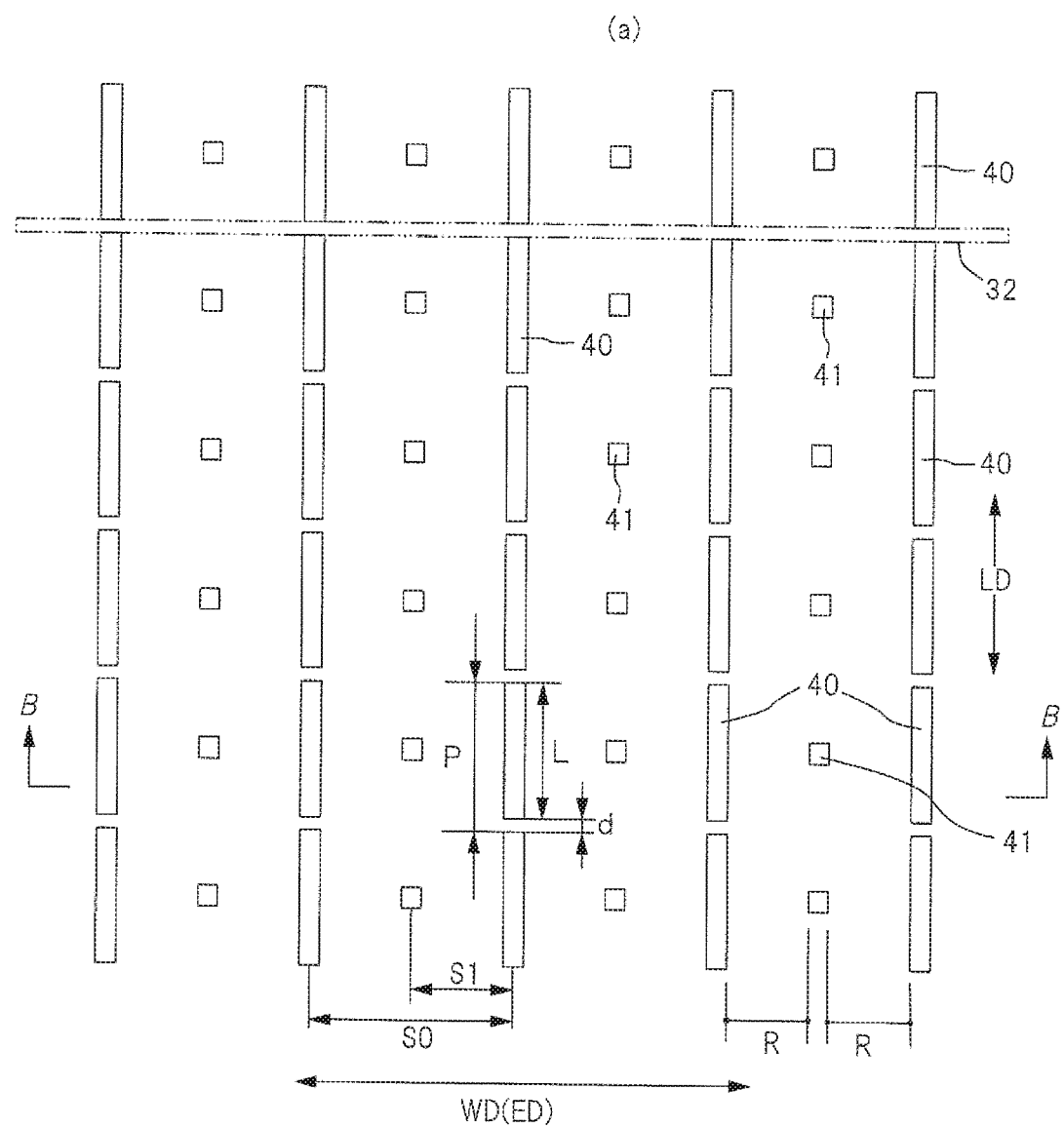
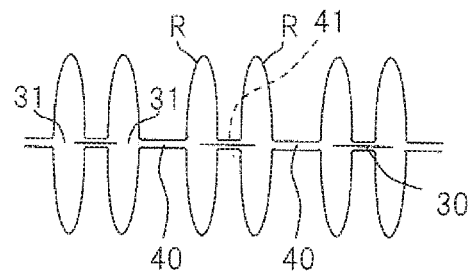

[FIG.13]
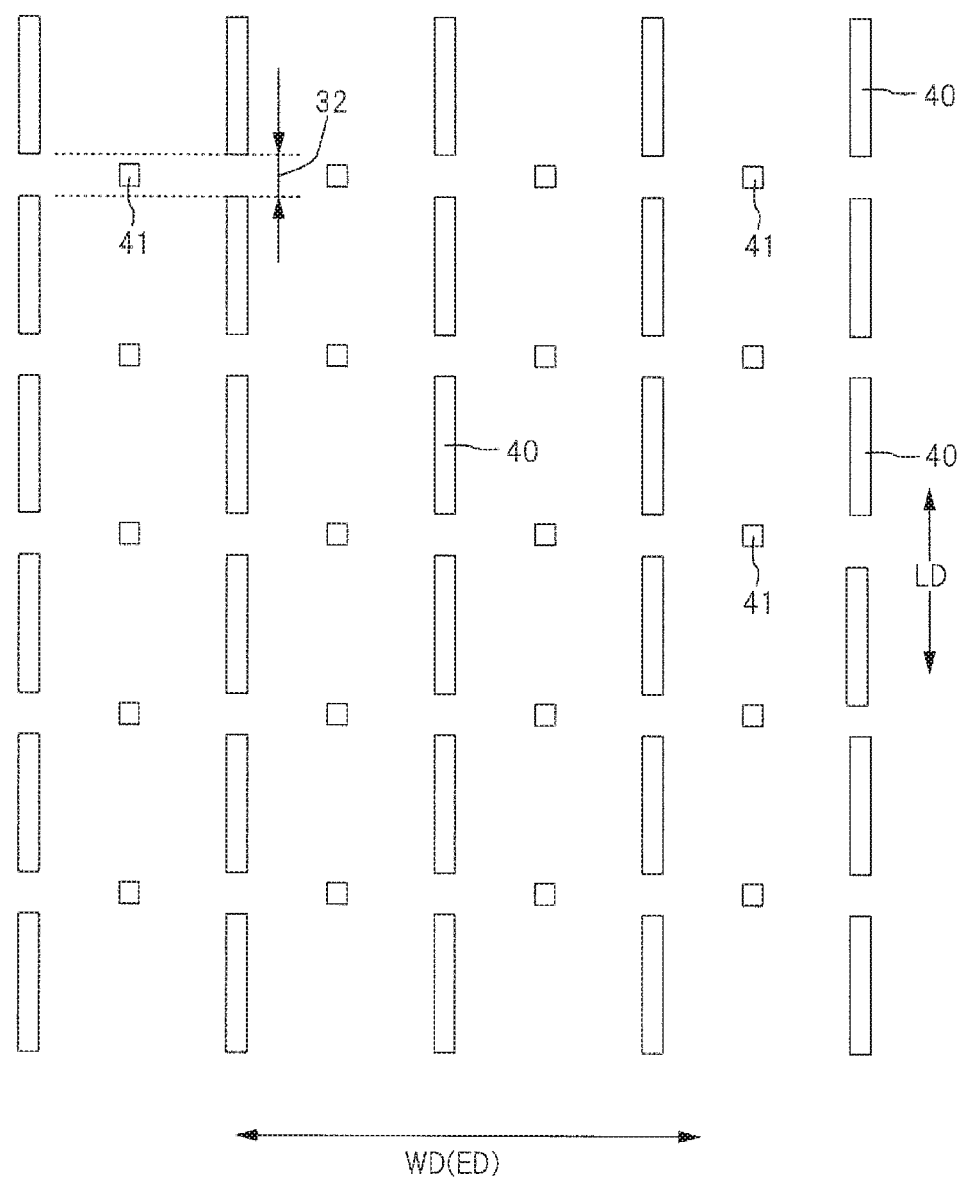

[FIG.14]
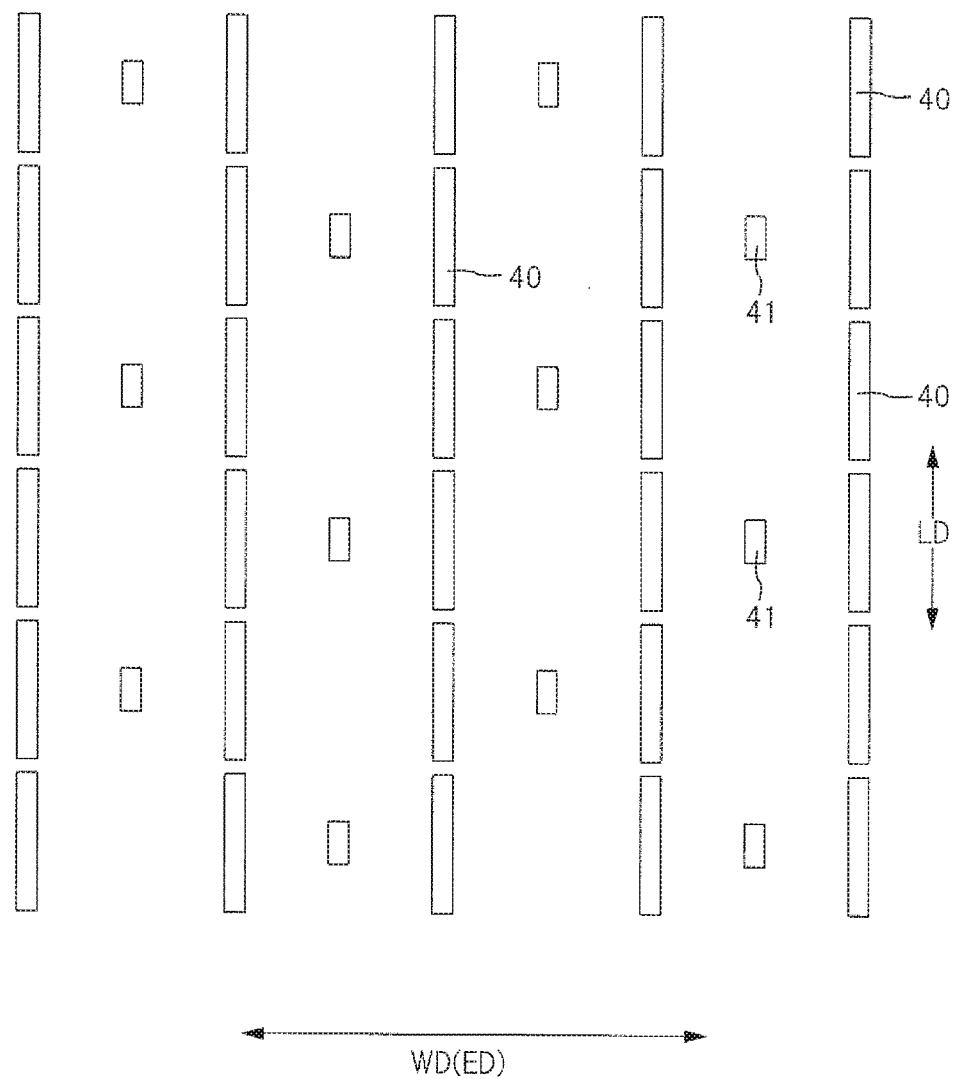

[FIG.15]
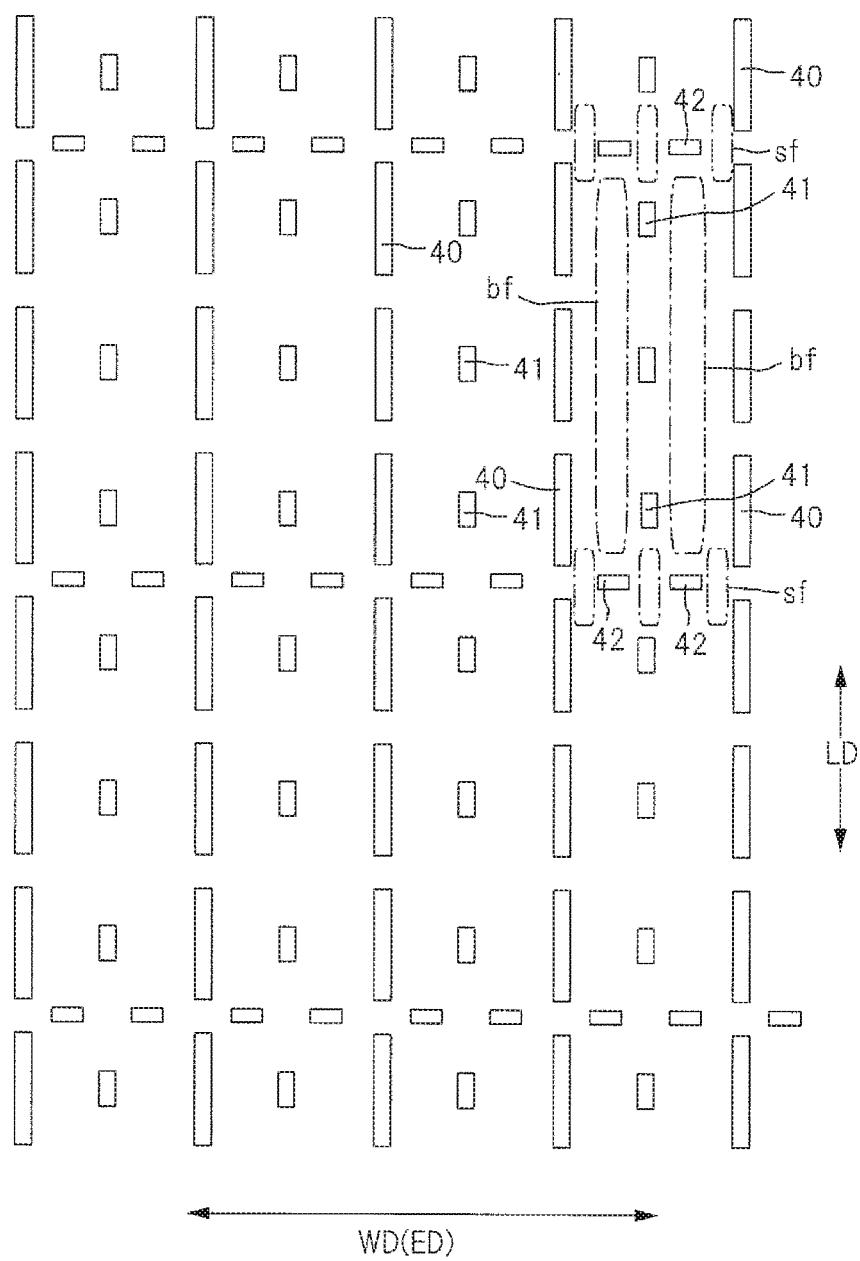

[FIG.16]
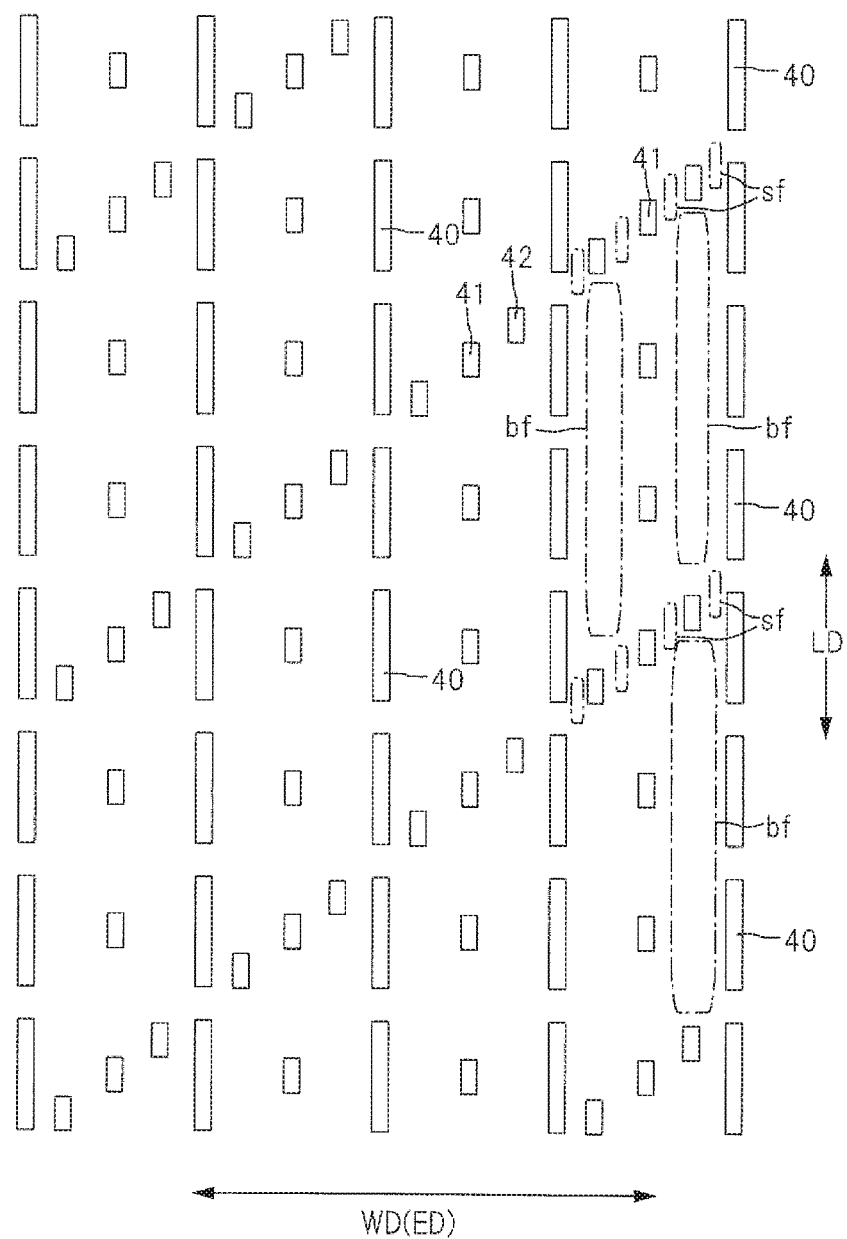

[FIG.17]
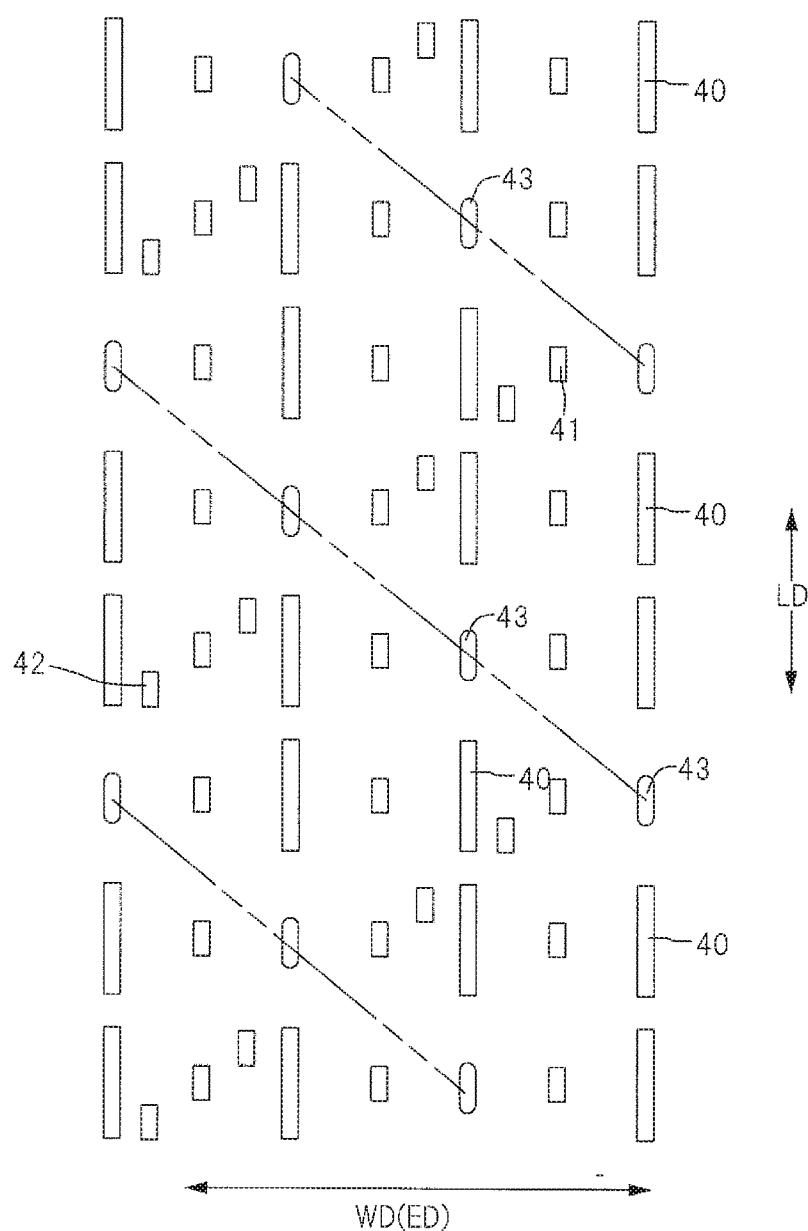

[FIG.18]
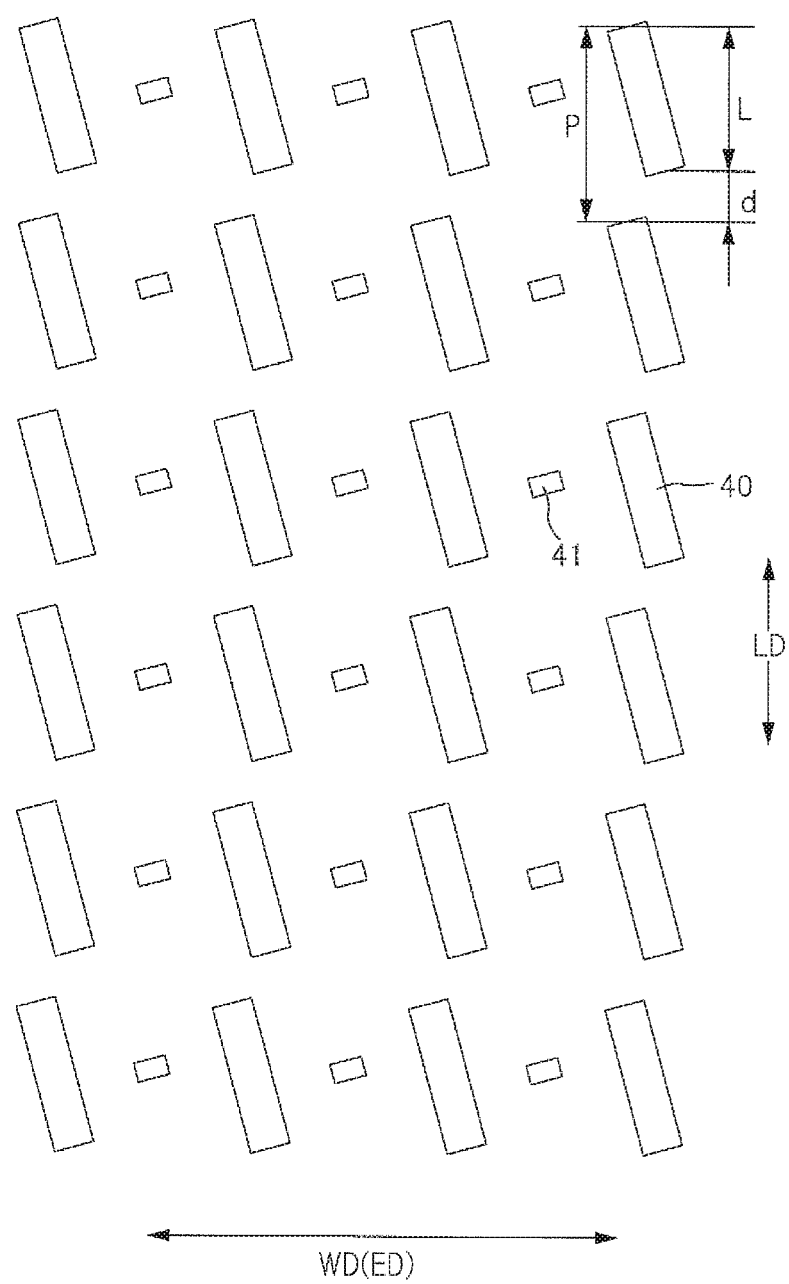

[FIG.19]
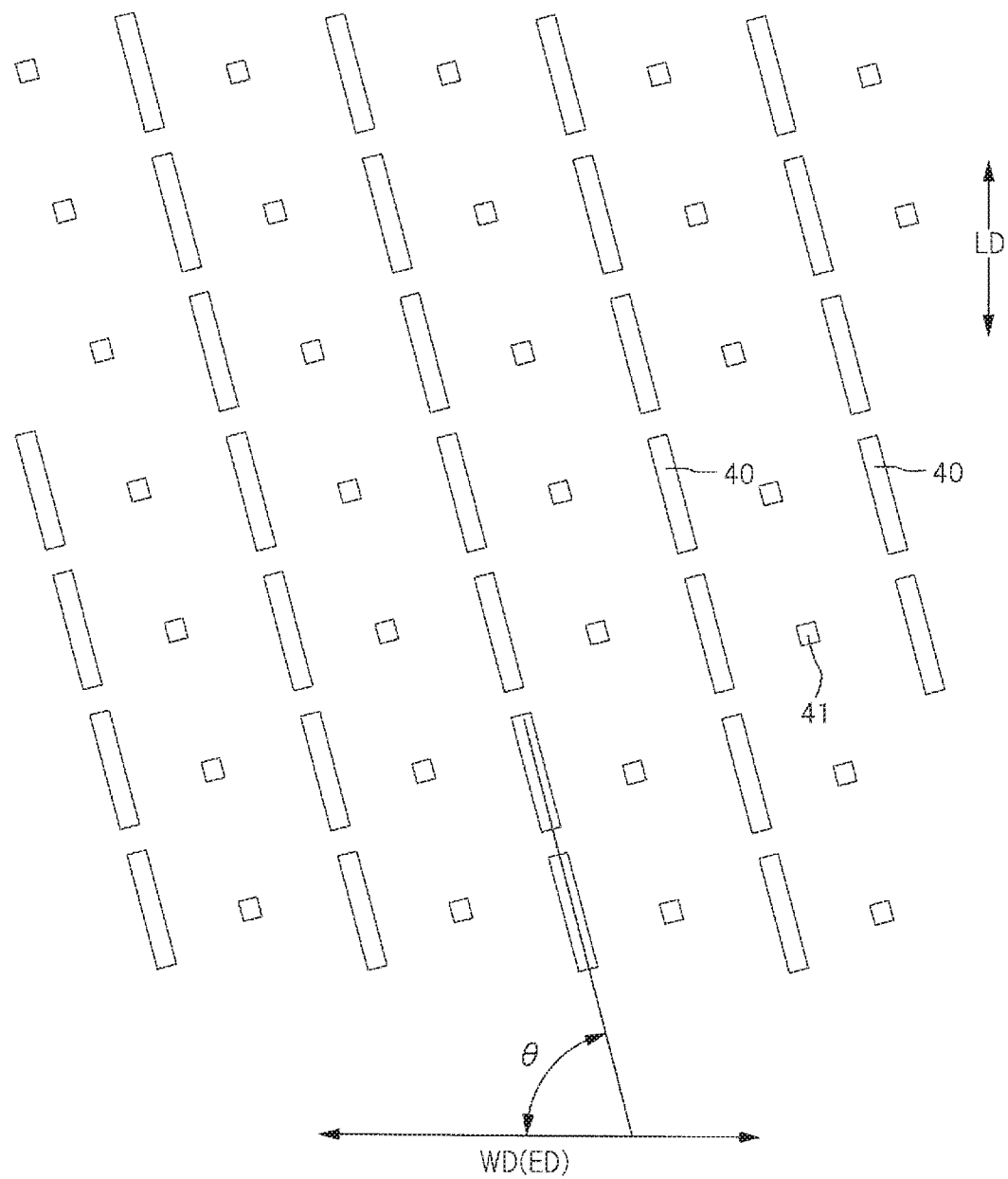

[FIG.20]
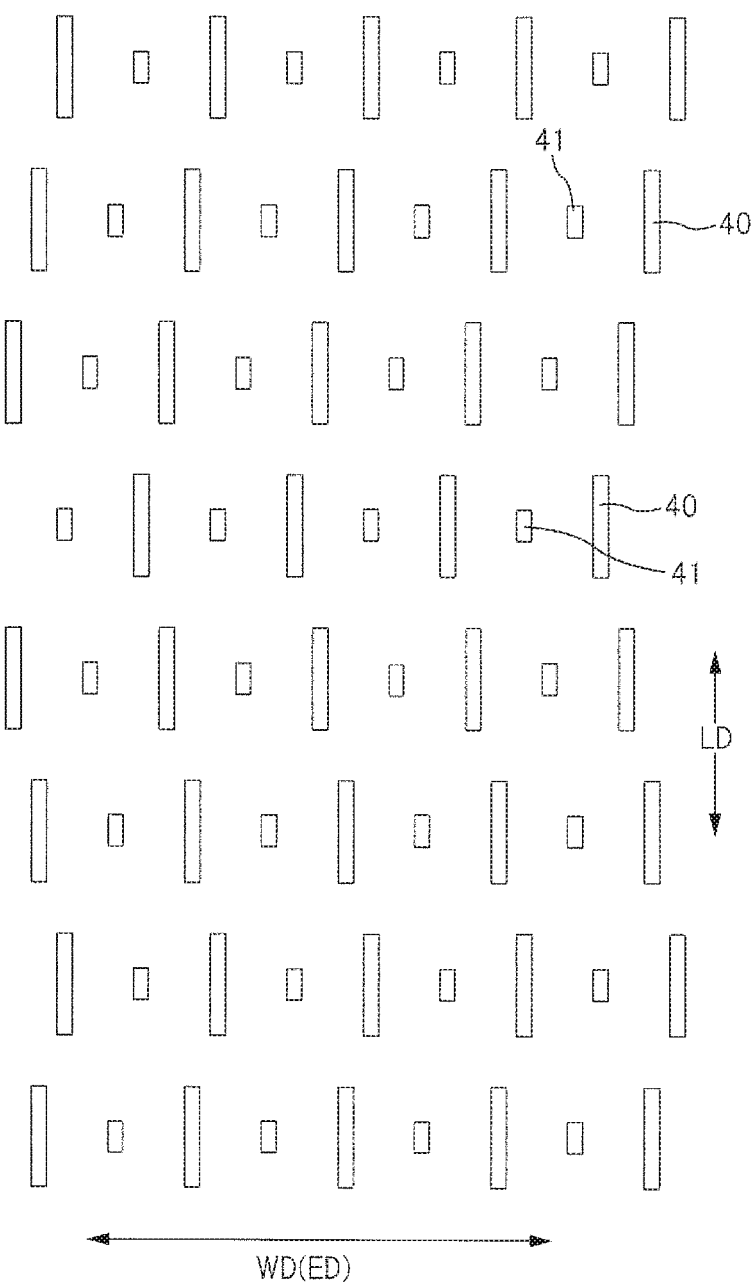

[FIG.21]
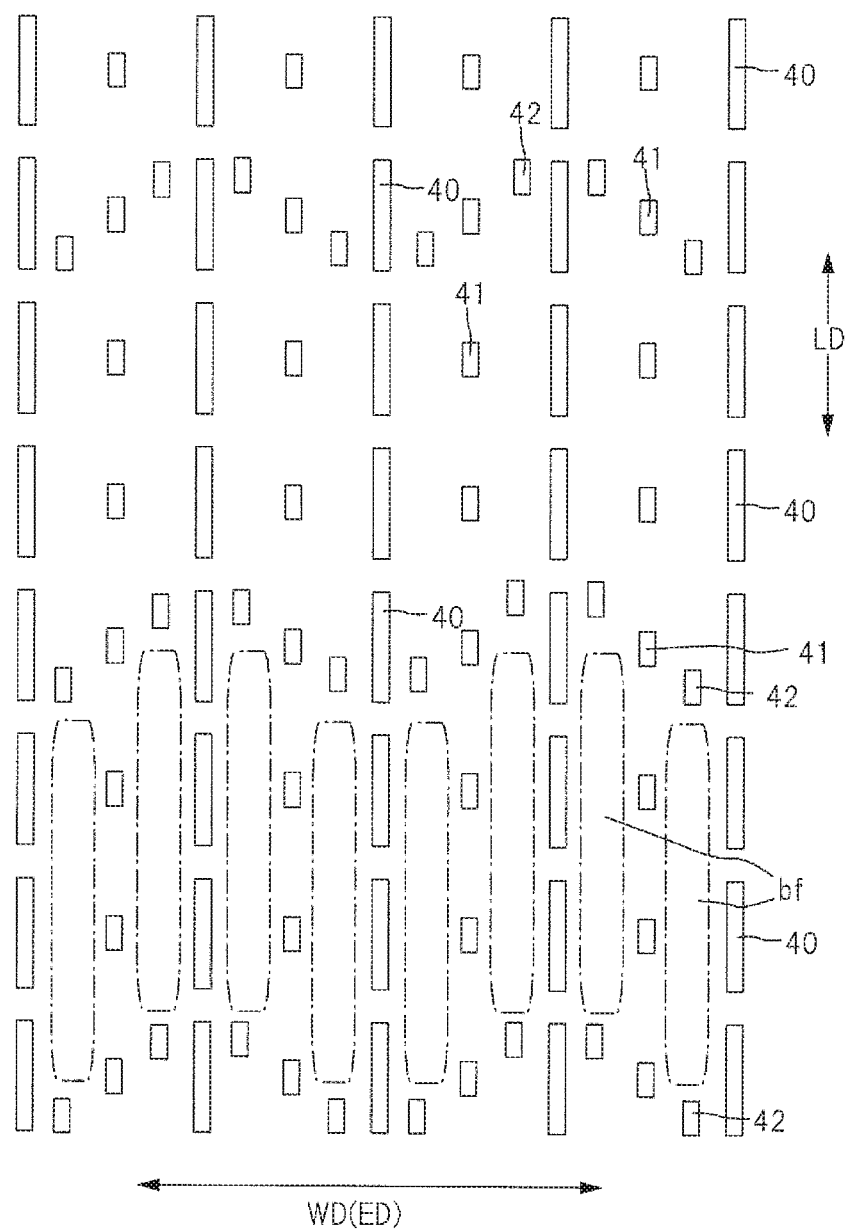

[FIG.22]
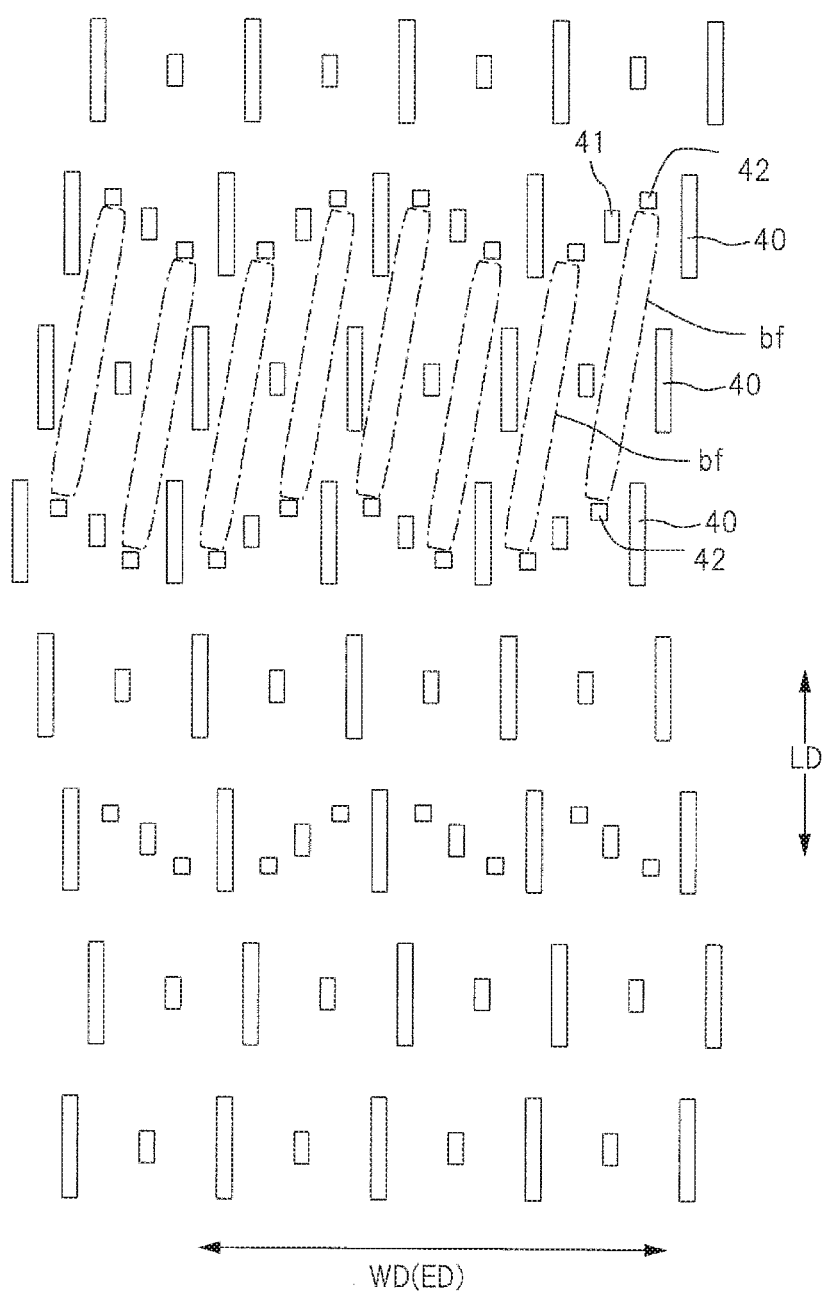

[FIG.23]
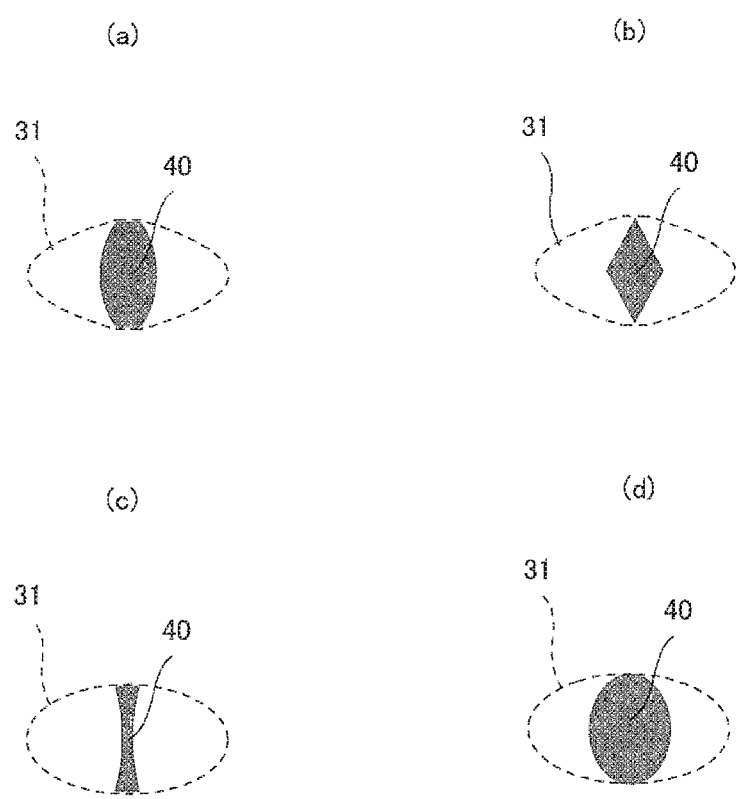

[FIG.24]
(a)
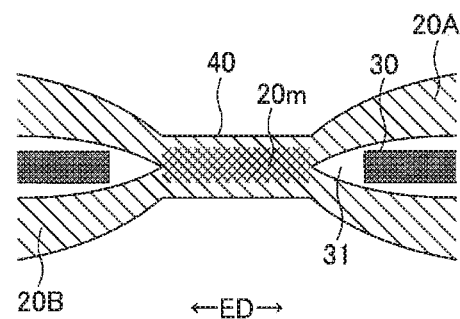
(b)
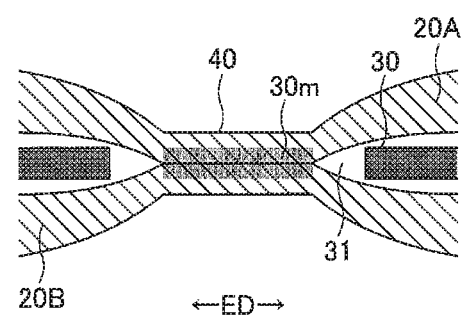
(c)
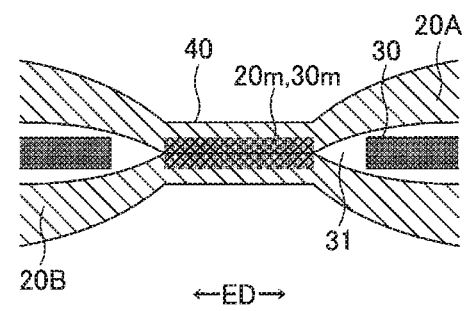

[FIG.25]
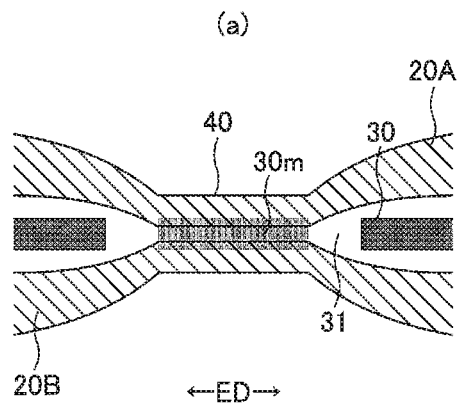
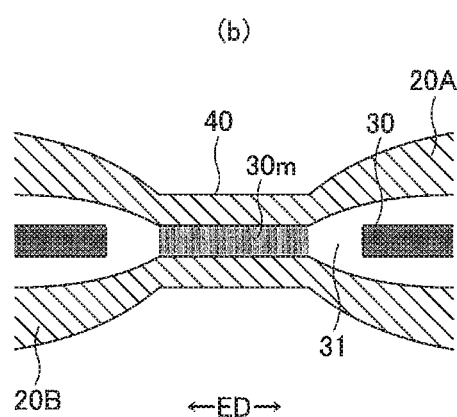
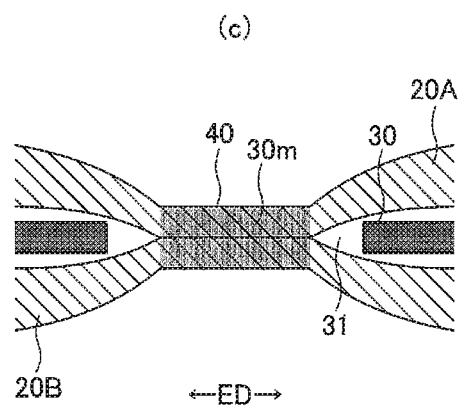

[FIG.26]
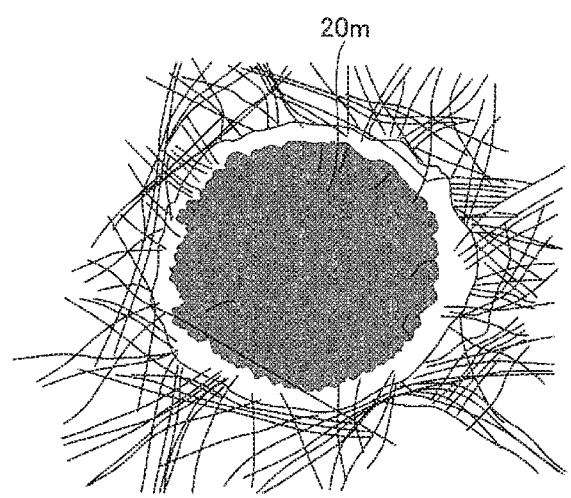
(b)
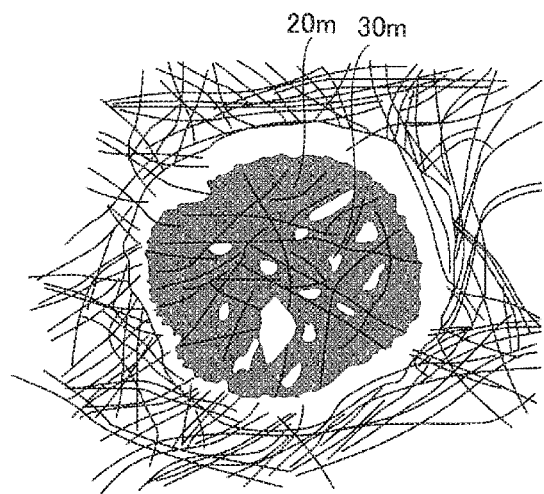

[FIG.27]
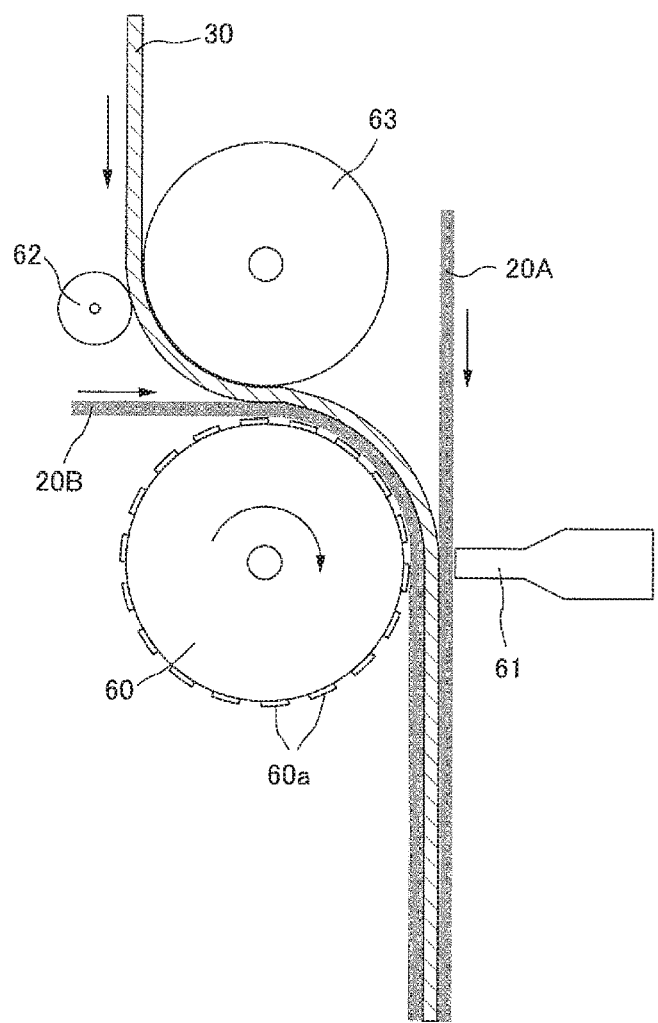

ELASTIC MEMBER AND DISPOSABLE WEARING ARTICLE INCLUDING ELASTIC MEMBER

CROSS-REFERENCE TO RELATED APPLICATIONS

This application is the U.S. national stage application of International Application PCT/JP2018/031281, filed Aug. 24, 2018, which international application was published on Apr. 4, 2019, as International Publication WO 2019/065024 in the Japanese language. The International Application claims priority of Japanese Patent Application No. 2017-187179, filed Sep. 27, 2017. The international application and Japanese application are both incorporated herein by reference, in entirety.

TECHNICAL FIELD

The present invention relates to an elastic member having a stretchable structure in which an elastic sheet such as an elastic sheet is interposed between a first sheet layer and a second sheet layer, and a disposable wearing article including this elastic member.

BACKGROUND ART

In a disposable wearing article such as a disposable diaper, to improve fitting to a body surface, it is common to impart elasticity to an appropriate place such as around legs or around a waist. As a method of imparting elasticity, a method of attaching an elongated elastic member such as rubber thread in a state of being stretched in a longitudinal direction has been widely adopted. However, in the case of imparting elasticity at a certain width, a mode in which rubber threads are fixed in a state of being arranged side by side with an interval in the width has been adopted. In addition, as a method of obtaining an excellent fitting surface, a method of attaching an elastic sheet in a state of being stretched in a direction of imparting elasticity, including that proposed by the present applicant, has been proposed. (For example, see Patent Literature 1 and Patent Literature 2).

The stretchable structure by the elastic film (hereinafter also referred to as elastic sheet stretchable structure) is obtained when a stretchable region is formed by an elastic film stacked between a first sheet layer made of a nonwoven fabric and a second sheet layer made of a nonwoven fabric, and, in a state in which the elastic film is stretched in a stretchable direction along surfaces thereof, the first sheet layer and the second sheet layer are bonded by a plurality of dotted sheet joined portions arranged at intervals in the stretchable direction and a direction orthogonal thereto through joint holes penetrating the elastic film.

In such an elastic sheet stretchable structure, in a natural length state, the elastic film contracts between the sheet joined portions, so that the intervals between the sheet joined portions decrease, and contraction wrinkles are formed to extend in a direction intersecting the stretchable direction between the sheet joined portions in the first sheet layer and the second sheet layer.

On the contrary, during stretching, as the elastic film stretches between the sheet joined portions, the intervals between the sheet joined portions and the contraction wrinkles in the first sheet layer and the second sheet layer widen, and elastic stretching is allowed up to a fully unfolded state of the first sheet layer and the second sheet layer. This elastic sheet stretchable structure is advantageous in that surface fitting is excellent, there is no surface bonding between the first sheet layer and the second sheet layer, and the elastic film, the structure is significantly flexible due to extremely little bonding between the first sheet layer and the second sheet layer, and the joint holes of the elastic film contribute to improvement in air permeability in a thickness direction.

However, when the above-described conventional elastic sheet stretchable structure is adopted, stretching stress in the width direction is prone to be strong. For example, in the case of application to an underpants type disposable diaper, not a few wearers are excessively strongly tightened.

CITATION LIST

Patent Literature

Patent Literature 1: JP 5967736 B2
Patent Literature 2: JP 2015-204982 A

SUMMARY OF INVENTION

Technical Problem

Therefore, a main object of the invention is to provide an elastic member which has low stretching stress in the stretchable direction in the stretchable structure of the elastic sheet and is excellent in a feeling of wearing in the case of being applied to an absorbent article.

Solution to Problem

An elastic member of the invention solving the above-mentioned problems has an elastic sheet stretchable structure in which an elastic sheet is interposed between a first sheet layer having air permeability and a second sheet layer having air permeability, and the first sheet layer and the second sheet layer are bonded through joint holes penetrating the elastic sheet or via the elastic sheet at a plurality of sheet joined portions arranged at intervals, characterized in that a stretchable region exhibiting the elastic sheet stretchable structure is allowed to be stretched and contracted in a stretchable direction by a contraction force of the elastic sheet, the joined portions have first joined portions and second joined portions, a first joined portion row is formed such that the first joined portions are spaced along an alignment direction in which alignment is performed at an angle intersecting the stretchable direction in a range of 45 degrees to 135 degrees, the first joined portions in the first joined portion row are formed to have a length of 0.3 to 7.0 mm with respect to an orthogonal direction orthogonal to the stretchable direction, the first joined portion row is formed to have a formation pitch of 2.0 to 20.0 mm with respect to the stretchable direction, as a distance with respect to the orthogonal direction determined by a mutual relationship between the adjacent first joined portions in the first joined portion row, which is represented by a ratio of (a separation distance between adjacent first joined portions)/(a distance from one point of a joined portion to one corresponding point of an adjacent first joined portion) is 5 to 60% in percentage, a plurality of the first joined portion rows is formed at intervals in the stretchable direction, and a plurality of the second joined portions having a shorter length than a length of the first joined portions is formed in the alignment direction between the first joined portion rows.

In the stretchable structure of the elastic sheet of the invention, the stretching stress in the stretchable direction is low. Furthermore, the contraction wrinkles extending in the alignment direction (orthogonal direction) intersecting the stretchable direction are formed between the first joined portion rows in a preferable mode.

This fact will be further described later together with an embodiment.

In a desirable mode, a plurality of second joined portion rows in which the second joined portions are spaced in the alignment direction is formed between the first joined portion rows.

When the second joined portion rows are formed, the contraction wrinkles are repeated in the alignment direction in the second joined portion rows, so that aesthetics is excellent in appearance.

Further, in a more preferable mode, a joined portion having the length of the first joined portions or a longer length is not formed in the second joined portion rows.

When the joined portion having the length of the first joined portions or a longer length is formed in the second joined portion rows, the stretching stress in the stretchable direction is low, and a length range of a bonded portion thereof becomes a non-formation range of wrinkles, which causes a degradation of appearance.

On the other hand, in a mode in which such a joined portion is not formed, the stretching stress in the stretchable direction is low, and a sufficiently long contraction wrinkles are formed in the alignment direction. Thus, an elastic member or absorbent article having excellent aesthetics and flexibility is strongly demanded.

The elastic member according to the invention can be incorporated as a member of a disposable wearing article.

Advantageous Effects of Invention

As described above, according to the invention, in the stretchable structure of the elastic sheet, the stretching stress in the stretchable direction is low, and the feeling of wearing is excellent when this elastic member is applied to a disposable wearing article.

BRIEF DESCRIPTION OF DRAWINGS

FIG. 1 is a plan view (internal surface side) of an underpants-type disposable diaper in an unfolded state.

FIG. 2 is a plan view (external surface side) of the underpants-type disposable diaper in the unfolded state.

FIG. 3 is a plan view illustrating only a main part of the underpants-type disposable diaper in the unfolded state.

FIG. 4(a) is a cross-sectional view taken along C-C line of FIG. 1, and FIG. 4(b) is a cross-sectional view taken along E-E line of FIG. 1.

FIG. 5 is a cross-sectional view taken along A-A line of FIG. 1.

FIG. 6 is a cross-sectional view taken along B-B line of FIG. 1.

FIG. 7 is a plan view (internal surface side) of a main part of a stretchable region in the underpants-type disposable diaper in the unfolded state.

FIG. 8(a) is a cross-sectional view corresponding to C-C line of FIG. 1, and FIG. 8(b) is a cross-sectional view corresponding to E-E line of FIG. 1.

FIG. 9 is a plan view and a cross-sectional view illustrating joined portion arrangement disclosed by Patent Literature 1.

FIG. 10 is a plan view illustrating joined portion arrangement disclosed by Patent Literature 2.

FIG. 11 is a plan view illustrating joined portion arrangement as a reference example for description.

FIG. 12 illustrates a first example of joined portion arrangement of the invention, in which FIG. 12(a) is a plan view and FIG. 12(b) is a cross-sectional view taken along B-B line.

FIG. 13 is a plan view illustrating a second example of joined portion arrangement of the invention.

FIG. 14 is a plan view illustrating a third example of joined portion arrangement of the invention.

FIG. 15 is a plan view illustrating a fourth example of joined portion arrangement of the invention.

FIG. 16 is a plan view illustrating a fifth example of joined portion arrangement of the invention.

FIG. 17 is a plan view illustrating a sixth example of joined portion arrangement of the invention.

FIG. 18 is a plan view illustrating a seventh example of joined portion arrangement of the invention.

FIG. 19 is a plan view illustrating an eighth example of joined portion arrangement of the invention.

FIG. 20 is a plan view illustrating a ninth example of joined portion arrangement of the invention.

FIG. 21 is a plan view illustrating a tenth example of joined portion arrangement of the invention.

FIG. 22 is a plan view illustrating an eleventh example of joined portion arrangement of the invention.

FIG. 23 is a plan view illustrating a twelfth example of joined portion arrangement of the invention.

FIG. 24 is a cross-sectional view illustrating a bonding mode example in joined portions of the invention.

FIG. 25 is a cross-sectional view for description illustrating the bonding mode example.

FIG. 26 is a plan view illustrating the bonding mode example.

FIG. 27 is a schematic view of an ultrasonic sealing device for manufacturing an elastic member.

DESCRIPTION OF EMBODIMENTS

Hereinafter, an embodiment of the invention will be described in detail with reference to accompanying drawings. Incidentally, a dotted pattern portion in a cross-sectional view illustrates bonding means such as a hotmelt adhesive.

FIG. 1 to FIG. 6 illustrate an underpants-type disposable diaper as an example of a disposable wearing article of the invention. A reference character LD (longitudinal direction) denotes a front-back direction, and a reference character WD denotes a width direction.

The underpants-type disposable diaper (hereinafter also simply referred to as a diaper) includes an outer member 20 forming a front body F and a back body B, and an inner member 10 fixed to and integrated with an inner surface of the outer member 20, and the inner member 10 is formed by interposing an absorbent body 13 between a liquid pervious top sheet 11 and a liquid impervious sheet 12. In manufacturing, after a back surface of the inner member 10 is bonded to the inner surface (upper surface) of the outer member 20 by bonding means such as a hotmelt adhesive, the inner member 10 and the outer member 20 are folded at a center in the front-back direction LD (longitudinal direction) corresponding to a boundary between the front body F and the back body B, and both side portions thereof are bonded to each other by thermal welding or the hotmelt adhesive to form side seal portions 21, thereby obtaining the underpants-type disposable diaper in which a waist opening and a pair of right and left leg openings are formed.

(Structure Example of Inner Member)

As illustrated in FIG. 4 to FIG. 6, the inner member 10 has a structure in which the absorbent body 13 is interposed between the liquid pervious top sheet 11 and the liquid impervious sheet 12 made of polyethylene, etc. and absorbs and holds excretion fluid passing through the top sheet 11. A planar shape of the inner member 10 is not particularly limited. However, a substantially rectangular shape is generally adopted as illustrated in FIG. 1.

As the liquid pervious top sheet 11 that covers the front surface side (skin side) of the absorbent body 13, a perforated or non-perforated nonwoven fabric, a porous plastic sheet, etc. is preferably used. As a material fiber constituting the nonwoven fabric, it is possible to adopt a regenerated fiber such as rayon and cupra or a natural fiber such as cotton in addition to a polyolefin-based synthetic fiber such as polyethylene or polypropylene, a polyester-based synthetic fiber, a polyamide-based synthetic fiber, etc., and it is possible to use a nonwoven fabric obtained by an appropriate processing method such as a spunlace method, a spunbond method, a thermal bond method, a meltblown method, a needle punch method, etc. Among these processing methods, the spunlace method is excellent in terms of flexibility and drape, and the thermal bond method is excellent in terms of being bulky and soft. When a large number of through-holes are formed in the liquid pervious top sheet 11, urine, etc. is quickly absorbed, and a dry touch property is excellent. The liquid pervious top sheet 11 is wound around a side edge portion of the absorbent body 13 and extends to a back surface side of the absorbent body 13.

As the liquid impervious sheet 12 that covers the back surface side (non-skin contact side) of the absorbent body 13, a liquid impervious plastic sheet such as polyethylene or polypropylene is used. However, in recent years, a sheet having a moisture penetration property is preferably used from a viewpoint of preventing stuffiness. For example, this water-impervious and moisture-permeable sheet is a microporous sheet obtained by melt-kneading an inorganic filler in an olefin resin such as polyethylene or polypropylene to form a sheet, and then stretching the sheet in a uniaxial or biaxial direction.

As the absorbent body 13, it is possible to use a known one, for example, a pulp fiber stack, an assembly of filaments of cellulose acetate, etc., or a nonwoven fabric-based body mixed with a high-absorbent polymer as necessary and fixed. To hold the shape and the polymer, the absorbent body 13 can be wrapped in a package sheet 14 having a liquid pervious and liquid retaining property such as crepe paper as necessary.

The absorbent body 13 is formed into a substantially hourglass shape having a narrower portion 13N narrower than both front and back sides at a crotch portion. A size of the narrower portion 13N can be determined as appropriate. A length of the narrower portion 13N in the front-back direction can be set to about 20 to 50% of a maximum length of the diaper, and a width of a narrowest portion thereof can be set to about 40 to 60% of a maximum width of the absorbent body 13. In the case of having such a narrower portion 13N, when the planar shape of the inner member 10 is substantially rectangular, non-absorbent body side portions 17 not having the absorbent body 13 are formed at a portion corresponding to the narrower portion 13N of the absorbent body 13 in the inner member 10.

The liquid impervious sheet 12 is folded back to the back surface side on both sides of the absorbent body 13 in the width direction together with the liquid pervious top sheet 11. As this liquid impervious sheet 12, it is desirable to use an opaque sheet so that brown color of excreta or urine is not seen. As opacification, a pigment or a filler such as calcium carbonate, titanium oxide, zinc oxide, white carbon, clay, talc, or barium sulfate added to plastic and formed into a film is preferably used.

Three-dimensional gathers 90 fit around the legs are formed on both side portions of the inner member 10. As illustrated in FIG. 5 and FIG. 6, each of the three-dimensional gathers 90 includes a fixed portion 91 fixed to a side portion of the back surface of the inner member 10, a main unit section 92 extending from the fixed portion 91 up to a side portion of the front surface of the inner member 10 through a side of the inner member 10, a fallen portion 93 formed by front and back end portions of the main unit section 92 fixed to the side portion of the front surface of the inner member 10 (top sheet 11 in the illustrated embodiment) in a fallen state, and a free portion 94 formed between parts of the fallen portion 93 which are not fixed. Each of these portions is formed of a gather sheet 95 that is a duplicate sheet obtained by folding a sheet such as a nonwoven fabric. The gather sheet 95 is attached over the entire inner member 10 in the front-back direction, the fallen portion 93 is provided on the front side and the back side of each of the non-absorbent body side portions 17, and the free portion 94 extends to both the front and back sides of the non-absorbent body side portion 17. In addition, between the double gather sheets 95, elongated gather elastic members 96 are disposed at tip portions of the free portion. As illustrated in FIG. 5, the gather elastic members 96 are for raising the free portion 94 by an elastic contraction force in a product state.

In an embodiment illustrated in FIG. 5 and FIG. 6, in portions other than fallen non-stretchable portions 97, the gather elastic members 96 are attached and fixed to the gather sheets 95 through a hotmelt adhesive at positions of the gather elastic members 96, and facing surfaces of the gather sheets 95 are bonded to each other. However, in the fallen non-stretchable portions 97, the hotmelt adhesive is not present at the positions of the gather elastic members 96. Therefore, the gather elastic members 96 and the gather sheets 95 are not attached to each other, and the facing surfaces of the gather sheets 95 are not bonded to each other at positions having the gather elastic members 96.

Each of the three-dimensional gathers 90 illustrated in FIG. 5 and FIG. 6 has a form in which the main unit section 92 is not folded back.

As the gather elastic members 96, it is possible to use normally used materials such as polystyrene-based rubber, polyolefin-based rubber, polyurethane-based rubber, polyester-based rubber, polyurethane, polyethylene, polystyrene, styrene-butadiene copolymer, silicone, polyester, etc. In addition, to make it difficult to see from the outside, it is preferable that a fineness is set to 925 dtex or less, a tension is set to 150 to 350%, and an interval is set to 7.0 mm or less. Incidentally, as the gather elastic members 96, it is possible to use a tape-like member having a certain width in addition to a thread-like member as in the illustrated embodiment.

As a material fiber constituting the gather sheets 95 described above, similarly to the liquid pervious top sheet 11, it is possible to adopt a regenerated fiber such as rayon or cupra or a natural fiber such as cotton in addition to a polyolefin-based synthetic fiber such as polyethylene or polypropylene, a polyester-based synthetic fiber, a polyamide-based synthetic fiber, etc., and it is possible to use a nonwoven fabric obtained by an appropriate processing method such as a spunbond method, a thermal bond method, a meltblown method, a needle punch method, etc. However, in particular, in order to prevent stuffiness, it is preferable to use a nonwoven fabric that suppresses a basis weight and has excellent air permeability. Further, with regard to the gather sheets 95, to prevent passage of urine, etc., prevent a rash, and enhance a feel to a skin (dry feeling), it is preferable to use a water repellent nonwoven fabric coated with a silicone-based, paraffin metal-based, or alkylchromic chloride-based water repellent agent, etc.

As illustrated in FIG. 3 to FIG. 6, the back surface of the inner member 10 is bonded to the inner surface of the outer member 20 by a hotmelt adhesive, etc. in an inner/outer fixing region 10B (shaded region). The inner/outer fixing region 10B may be determined as appropriate and may correspond to almost the entire inner member 10 in a width direction WD. However, it is preferable that both ends in the width direction are not fixed to the outer member 20.

(Structure Example of Outer Member)

The outer member 20 extends to the outside of side edges of the absorbent body 13. Referring to the outer member 20, as in the illustrated embodiment, in a crotch portion, side edges of the outer member 20 may be located on a central side of side edges of the inner member 10 in the width direction or located on an outer side thereof in the width direction. In addition, the outer member 20 includes lower torso portions T which are front-back direction ranges corresponding to the side seal portions 21 and an intermediate portion L which is a front-back direction range between the lower torso portion T of the front body F and the lower torso portion T of the back body B.

Further, the outer member 20 of the illustrated embodiment has an elastic sheet stretchable structure 20X in which an elastic sheet, for example, an elastic film 30 is interposed between the first sheet layer 20A and the second sheet layer 20B as illustrated in FIG. 2 and FIG. 4 to FIG. 6 except for a middle of the intermediate portion L in the front-back direction and the first sheet layer 20A and the second sheet layer 20B are bonded through joint holes 31 penetrating the elastic film 30 at a plurality of sheet joined portions 40 arranged at intervals as illustrated in FIG. 9.

In an embodiment of application to the diaper, a stretchable direction ED of the elastic sheet (the elastic film 30 in an example of FIG. 9) is regarded as the width direction WD of the diaper.

The first sheet layer 20A and the second sheet layer 20B may be indirectly bonded through the elastic film 30 instead of through the joint holes 31 of the elastic film 30. A planar shape of the outer member 20 is formed by concave around-leg lines 29 so that both side edges of the intermediate portion L in the width direction form leg openings, respectively, and has a shape similar to an hourglass as a whole. The outer member 20 may be formed separately in the front body F and the back body B, and both bodies may be disposed to be separated in the front-back direction LD of the diaper at the crotch portion.

An embodiment illustrated in FIG. 1 and FIG. 2 is an embodiment in which the elastic sheet stretchable structure 20X extends up to waist end portions 23. However, if necessary, for example, if tightening of the waist end portions 23 is insufficient when the elastic sheet stretchable structure 20X is used for the waist end portions 23, the stretchable structure may be provided by conventional elongated waist portion elastic members 24 without providing the elastic sheet stretchable structure 20X in the waist end portions 23 as illustrated in FIG. 7 and FIG. 8. The waist portion elastic members 24 are elongated elastic members such as a plurality of rubber threads disposed at intervals in the front-back direction LD, and apply a stretching force to tighten a waist of a body. The waist portion elastic members 24 are not disposed substantially in a bundle at close intervals, and three or more waist portion elastic members 24, preferably five or more waist portion elastic members 24 are disposed at intervals of about 3 to 8 mm in the front-back direction to form a predetermined stretchable zone. A stretch rate the waist portion elastic members 24 at the time of fixing can be determined as appropriate, and may be set to about 230 to 320% for a normal adult. As the waist portion elastic members 24, rubber threads are used in the illustrated example. However, other elongated elastic members such as flat rubber may be used. Although not illustrated, the elastic film 30 may be provided at the waist end portions 23, and the elongated waist portion elastic members 24 may be provided at positions overlapping the elastic film 30, so that a stretchable structure using both elastic members can be provided. In addition, in the illustrated embodiment, the elongated elastic members extending along leg openings are not provided at edge portions of the leg openings in the outer member 20. However, the elongated elastic members may be provided at positions overlapping the elastic film 30 at the edge portions or instead of the elastic film 30 at the edge portions.

As other embodiments, although not illustrated, appropriate modifications can be made. For example, the elastic sheet stretchable structure 20X may not be provided in the intermediate portion L between the lower torso portion T of the front body F and the lower torso portion T of the back body B, the elastic sheet stretchable structure 20X may be continuously provided in the front-back direction LD from the inside of the lower torso portion T of the front body F to the inside of the lower torso portion T of the back body B via the intermediate portion L, or the elastic sheet stretchable structure 20X may be provided only in one of the front body F and the back body B.

(Embodiment of Joined Portions)

The invention has a characteristic in arrangement of the joined portions. To clarify this characteristic, arrangement of joined portions of a conventional example will be described in detail.

FIG. 9 is illustrated as a representative example for Patent Literature 1.

In more detail, a group of the joined portions 40 has staggered arrangement, the joined portions 40 are elongated in a direction orthogonal to the stretchable direction and in line symmetry with respect to a center line passing through a center in the stretchable direction (lateral symmetry in FIG. 9(a)), a width 40x of each of the joined portions 40 in the stretchable direction is preferably set to 0.2 to 0.4 mm, an interval d1 between the joined portions 40 arranged in the stretchable direction is set to 3 to 12.9 mm, more preferably 5 to 6.4 mm, and an interval d2 between the joined portions 40 arranged in the direction orthogonal to the stretchable direction is set to 2 to 10.5 mm, more preferably 2.3 to 4.6 mm.

As described above, the joined portions 40 having the remarkably narrow width 40x in the stretchable direction are arranged in a staggered manner at the separation interval d1 which is somewhat wide in the stretchable direction, the contraction force of the elastic film 30 directly acts on each of the joined portions 40, and arrangement and intervals of the respective joined portions 40 are firmly maintained at the positions of the joint holes 31 of the elastic film 30. As a result, flexibility is unlikely to decrease. In addition, pleats 25f extend almost straight along the direction orthogonal to the stretchable direction, and each of the joined portions 40 is hidden between the pleat 25f and the pleat 25f and are not noticeable. Therefore, the elastic sheet stretchable structure 20X having an appearance closer to that of cloth is obtained while suppressing a decrease in flexibility.

On the other hand, when the joined portion 40 has a circular shape even though arrangement of the joined portions 40 corresponds to staggered arrangement, the joined portion 40 is clearly visible between the pleat 25f and the pleat 25f in wrinkles, and the pleats 25f extend in the direction orthogonal to the stretchable direction by largely going around the joined portions 40. Thus, wavy pleats 25f are formed as a whole, and there is a tendency that a cloth-like appearance may not be obtained.

From such a viewpoint, it is desirable that the shape of the joined portion 40 is elongated in the direction orthogonal to the stretchable direction. However, when a maximum length of the joined portion 40 in the direction orthogonal to the stretchable direction is excessively short or excessively long, there is concern that linearity of the pleats 25f may be lowered or flexibility may be lowered. Therefore, even though these dimensions can be determined as appropriate, it is preferable that a length 40y of the joined portion 40 in the direction orthogonal to the stretchable direction is 0.4 to 3.2 mm, particularly 0.7 to 1.4 mm.

On the other hand, in Patent Literature 2, arrangement of openings of the elastic film (illustrated as slightly vertically long rectangles) is staggered arrangement in both the two examples illustrated in FIGS. 10(a) and 10(b), and small circular sub-joined portions are disposed between rectangular main openings in the example of FIG. 10(b). The example of FIG. 10(b) is based on an idea of staggered arrangement.

Further, arrangement and dimensions of the respective openings are preferably in the dimension ranges (unit is mm) described in FIG. 10 mainly from viewpoints of appearance, texture, air permeability, etc.

Both inventions of Patent Literatures 1 and 2 disclose vertically long openings and staggered arrangement.

However, in the conventional example, since the separation interval between the openings of the elastic film in the direction orthogonal to the stretchable direction is set to be large, the stretching stress in the stretchable direction is high. For example, in the case of application to an underpants type disposable diaper, not a few wearers feel that the wearers are excessively strongly tightened (in the width direction).

Here, the opening length B is set to 0.3 to 0.7 mm, and the separation interval H is set to 0.6 to 1.4 mm. When these figures are used to calculate the percentage of (separation distance between adjacent first joined portions)/(distance from one point of a joined portion to one corresponding point of an adjacent first joined portion) according to the invention, (0.3 to 0.7 mm)/(0.6 to 1.4 mm)=21.4 to 183% is obtained. Even though a lower limit in the calculation is small, it is considered that a large value is assumed in reality.

On the other hand, the inventors have found that when the separation interval between the openings of the elastic film in the direction orthogonal to the stretchable direction (up-down direction in the figure: direction of reference character LD) is set to be small as illustrated in FIG. 11, the stretching stress in the stretchable direction can be decreased, and thus the diaper can be gently fit to the wearer by a weak tightening force in the case of application to the underpants type disposable diaper.

A reason therefor is considered to be as follows. The openings open in the width direction to become the joint holes 31 as illustrated in FIG. 9 merely by applying a small stretching force in the width direction (stretchable direction of the elastic film) from the outside. On the other hand, since the openings are not present in a separation interval region orthogonal to the stretchable direction between the openings, even when stretched in the width direction, the stretching stress of the elastic film acts as the contraction force without change to tighten the wearer.

An embodiment illustrated in FIG. 11 can easily fit the diaper to the wearer, and has an advantage that air permeability is excellent since a ratio of an area occupied by the joined portions and a ratio of an area occupied by the joint holes in a use state of being stretched in the width direction increase.

However, in a usage mode in a product of the embodiment illustrated in FIG. 11(a), a wrinkle along an orthogonal direction LD is formed in a separation region between a row of joined portions 40, 40 . . . along the orthogonal direction LD and a row of joined portions 40, 40 . . . separated from and adjacent to the row in the stretchable direction ED (width direction). As illustrated in FIG. 11(b), this wrinkle 25F simply has a uniform mountain shape. That is, this shape is shown in Patent Literature 1 and different from a cross section illustrated in FIG. 9(c).

When the embodiment illustrated in FIG. 11 is viewed from a viewpoint of design as the entire stretchable region of the product, the embodiment is prone to correspond to a simple design in which the wrinkle 25F long in the orthogonal direction LD is merely formed with uniform repetition in the stretchable direction ED (width direction), and product appeal is poor.

The invention has the first joined portion and a second joined portion, specifically has a configuration described in the claims, includes various modes, and includes a combination of various modes.

For convenience of paper width, typical examples will be sequentially described below.

First Example

An elastic member according to a first example illustrated in FIG. 12 has an elastic sheet stretchable structure in which an elastic sheet is interposed between a first sheet layer having air permeability and a second sheet layer having air permeability, and the first sheet layer and the second sheet layer are bonded through joint holes penetrating the elastic sheet or via the elastic sheet at a plurality of sheet joined portions arranged at intervals.

A stretchable region exhibiting the elastic sheet stretchable structure can be stretched in the stretchable direction by a contraction force of the elastic sheet.

In the invention, the joined portions have second joined portions 41, 41 . . . in addition to first joined portions 40, 40 . . . .

The first joined portions 40, 40 . . . are arranged at intervals along the orthogonal direction LD to form a first joined portion row.

For example, as will be described later with reference to FIG. 19 as an eighth example, the row of the first joined portions 40, 40 . . . may be inclined at an intersection angle θ with respect to the stretchable direction ED in a range of 45 degrees to 135 degrees without extending along the orthogonal direction LD.

The first example is an example in which the intersection angle θ is 90 degrees.

The first joined portion 40 is formed to have a length L of 0.3 to 7.0 mm, preferably 0.5 to 5.0 mm, particularly preferably 0.7 to 2.5 mm with respect to the orthogonal direction.

In addition, the row of the first joined portions 40, 40 . . . is formed so that a formation pitch S0 with respect to the stretchable direction ED is 2.0 to 20.0 mm, preferably 3.0 to 15.0 mm, particularly preferably 4.0 to 10.0 mm.

Furthermore, as a distance with respect to the orthogonal direction LD, defined by a mutual relationship between adjacent first joined portions 40 and 40 in the row of the first joined portions 40, 40 . . . , a percentage R of a ratio of (a separation distance d between adjacent first joined portions)/(a distance P from one point of a joined portion to one corresponding point of an adjacent first joined portion) is set to 5 to 60%, preferably 10 to 45%, particularly preferably 20 to 35%.

When this percentage is excessively high, in the case of application to a product, the stretching stress in the width direction (stretchable direction) is high, and it is difficult to obtain suitable fitting as a wearing article.

In addition, when the percentage is excessively low, a possibility that the first joined portions 40 and 40 adjacent to each other in the orthogonal direction LD are continuous in a manufacturing process may not be excluded, and more fundamentally, an anvil and a heating horn that form the joined portions are excessively burdened with equipment, which hinders stable operation.

It is desirable that a joined portion having the length L of the first joined portion 40 or a longer length is not formed in the row of the second joined portions 41 and 41. Also from this point of view, this embodiment is completely different from the embodiment of FIG. 10.

The first example exhibits typically the following advantages and features.

(1) Since the percentage R is low, an elastic sheet member having a low stretching stress in the stretchable direction and having a flexible elongation is obtained, and when this elastic sheet member is applied to an absorbent article, a feeling of wearing is excellent.

In addition, since an opening ratio is increased, the air permeability is increased.

(2) Since not only the row of the first joined portions 40, 40 . . . but also the row of the second joined portions 41, 41 . . . is formed, inter-row pleats R can be formed between the row of the first joined portions 40, 40 . . . and the row of the second joined portions 41, 41 . . . .

(3) The second joined portions 41 have a smaller area than that of the first joined portions 40, and thus look like a pattern.

(4) A statement that the inter-row pleats R can be formed between the row of the first joined portions 40, 40 . . . and the row of the second joined portions 41, 41 . . . means that two inter-row pleats can be formed between the row of the first joined portions 40, 40 . . . and the row of the first joined portions 40, 40 . . . . However, since a distance between the second joined portions 41 and 41 is long in the row of the second joined portions 41, 41 . . . , the statement means that pleats can be formed without excessively burdening the anvil and the heating horn with equipment. As a result, when compared to a case in which the inter-row pleats are formed only by the row of the first joined portions 40, 40 . . . as illustrated in FIG. 11, a large number of pleats can be formed with a narrow width per unit area without burdening the equipment.

Thus, a contact area of the wearer with the skin can be reduced, and comfort and softness can be improved.

Second Example

As illustrated in FIG. 13, a group of the second joined portions 41, 41 . . . can be disposed between the first joined portions 40 and 40 in the orthogonal direction LD. In this case, even when the length L of the first joined portion 40 is short, the second joined portions 41 are positioned, so that the stretching stress can be reduced.

Third Example

As illustrated in FIG. 14, for example, it is possible to adopt a mode in which one second joined portion 41 is disposed adjacent to two first joined portions 40 and 40 rather than arranging the second joined portion 41 adjacent to the first joined portion 40 on a one-to-one basis.

Fourth Example

As illustrated in FIG. 15, it is possible to form a row of third joined portions 42, 42 . . . having a long separation interval in the orthogonal direction LD between the row of the first joined portions 40, 40 . . . and the row of the second joined portions 41, 41 . . . .

By forming the third joined portion 42, it is possible to form large pleats bf obtained by dividing the inter-row pleats R shown in the first example in the orthogonal direction LD.

A small pleat sf can be formed between the third joined portion 42 and the row of the first joined portions 40, 40 . . . .

A pleat group obtained by dividing the inter-row pleats R has a low bending rigidity (easy to bend) of the elastic member and an excellent following ability with respect to movement of the body.

Fifth Example

As illustrated in FIG. 16, by obliquely arranging the positions of the third joined portions 42 together with the second joined portions 41, a group of large pleats bf in an oblique array can be formed, and designability is high.

Sixth Example

As illustrated in FIG. 17, fourth joined portions 43 can be inserted and disposed in the row of the first joined portions 40, 40 . . . . In this case, the fourth joined portions 43, 43 . . . can be disposed along the stretchable direction ED or obliquely as illustrated in the figure. In this case, the area of the fourth joined portion 43 is preferably 5% or more and 50% or less of the area of the first joined portion 40.

Seventh Example

As illustrated in FIG. 18, the first joined portions 40 may be inclined. The second joined portions 42 may be inclined.

In the invention, since the length of the joined portion is based on the orthogonal direction LD, as illustrated in FIG. 18, the length L of the first joined portion 40 corresponds to a length in the orthogonal direction LD from a center of one side to a central portion of the other side.

With regard to the separation interval, a distance in the orthogonal direction LD between a center of a side and a center of a side facing the side corresponds to the separation distance d.

Eighth Example

FIG. 19 illustrates an example in which both the first joined portions 40 and the second joined portions 42 are inclined, and each row of the joined portions is inclined at an intersection angle θ with respect to the stretchable direction ED in a range of 45 degrees to 135 degrees without extending along the orthogonal direction LD. The intersection angle θ is preferably 50 degrees to 130 degrees, particularly preferably 60 degrees to 120 degrees.

An advantage of this joined portion row inclined to intersect the stretchable direction ED without extending in the orthogonal direction LD is clear when the seventh example illustrated in FIG. 18 is compared. That is, in the example illustrated in FIG. 19, the fact that, for example, the separation interval between the first joined portions 40 and 40 on a line in the orthogonal direction LD is considerably larger than that of the seventh example illustrated in FIG. 18 brings a benefit.

That is, for example, it is desirable that the first sheet layer 20A and the second sheet layer 20B are bonded to each other in the sheet joined portions 40 using bonding means by material welding such as heat sealing or ultrasonic sealing.

In the case of continuous production, seal melting is performed between an anvil roll and an ultrasonic horn using ultrasonic waves. To prevent energy loss, it is important that the ultrasonic horn is in close contact with the sheet in the entire anvil roll in axial direction. In the case of forming a pattern having a large proportion of anvil roll convex such as the row of the joined portions 40, 40 . . . of FIG. 12 along a bus line in line contact for this purpose, it is necessary to output large ultrasonic waves. When an excessive tightening force is applied along the bus line in line contact for this purpose, a burden on an equipment side is large.

On the other hand, in the case of the eighth example illustrated in FIG. 19 (generally in the case of an inclined arrangement), a proportion occupied by the joined portions located on a line in the orthogonal direction LD is small, resulting in a stable linear pressure. Thus, the equipment burden is small, and stable operation can be performed.

In the eighth example illustrated in FIG. 19, since the first joined portions 40 (and the second joined portions 42) are inclined, there is an advantage that it is possible to form pleats excellent in designability.

Ninth Example

A ninth example illustrated in FIG. 20 adopts a mode in which the row of the first joined portions 40, 40 . . . and the row of the second joined portions 41, 41 . . . are arranged along a waveform curve that swings in the stretchable direction ED.

The arrangement of the waveform curve is excellent in aesthetics.

Tenth Example

A tenth example illustrated in FIG. 21 adopts a mode in which the large pleats bf are arranged along a waveform curve that swings in the orthogonal direction LD. The arrangement of this waveform curve is also excellent in aesthetics.

Eleventh Example

An eleventh example illustrated in FIG. 22 adopts a mode in which the row of the first joined portions 40, 40 . . . and the row of the second joined portions 41, 41 . . . are arranged along a waveform curve that swings in the stretchable direction ED, and the inclined large pleats bf are arranged along a waveform curve that swings in the orthogonal direction LD. The arrangement of this waveform curve allows formation of complex pleats and is excellent in aesthetics.

Furthermore, an embodiment of the invention will be described. The shapes of the individual sheet joined portions 40 and joint holes 31 in the natural length state can be determined as appropriate in addition to the above-described rectangle. For example, in addition to a convex lens shape (see FIG. 23(a)), a rhombus shape (see FIG. 23(b)), a concave lens shape (see FIG. 23(c)), and an elliptical shape (see FIG. 23(d)) as exemplified in FIG. 23, it is possible to adopt any shape such as a perfect circle, a triangle, a polygon, a star shape, a cloud shape, etc.

The joint holes 31 mainly relate to the shape of the joined portions 40 (41, 42, and 43) and a manufacturing stage or a degree of stretching/contraction.

When the first sheet layer 20A and the second sheet layer 20B are bonded in the sheet joined portions 40 through the joint holes 31 formed in the elastic film 30, it is desirable that the first sheet layer 20A and the second sheet layer 20B are not bonded to the elastic film 30 except at least between the first sheet layer 20A and the second sheet layer 20B in the sheet joined portions 40.

Bonding means for the first sheet layer 20A and the second sheet layer 20B in the sheet joined portions 40 is not particularly limited. For example, the first sheet layer 20A and the second sheet layer 20B may be bonded to each other in the sheet joined portions 40 using a hotmelt adhesive or using bonding means by material welding such as heat sealing or ultrasonic sealing.

In a case in which the first sheet layer 20A and the second sheet layer 20B are bonded through the joint holes 31 of the elastic film 30 in the sheet joined portions 40, as a mode in which the sheet joined portions 40 are formed by material welding, it is possible to adopt any one of a first welding mode in which the first sheet layer 20A and the second sheet layer 20B are bonded only by a molten and solidified material 20m of a most part or a part of at least one of the first sheet layer 20A and the second sheet layer 20B in the sheet joined portions 40 (see FIG. 24(a)), a second welding mode in which the first sheet layer 20A and the second sheet layer 20B are bonded only by a molten and solidified material 30m of all, a most part, or a part of the elastic film 30 in the sheet joined portions 40 (see FIG. 24(b)), and a third welding mode in which both of these modes are combined (see FIG. 24(c)), and the second and third welding modes are preferable.

A particularly preferable mode is that the first sheet layer 20A and the second sheet layer 20B are bonded by the molten and solidified material 20m of the part of the first sheet layer 20A and the second sheet layer 20B and the molten and solidified material 30m of all or the most part of the elastic film 30 in the sheet joined portions 40. Incidentally, in the third welding mode illustrated in FIG. 26(b), the molten and solidified material 30m of the elastic film 30 shown in white is seen between fiber molten and solidified materials 20m of the first sheet layer 20A or the second sheet layer 20B shown in black. On the other hand, in the first welding mode illustrated in FIG. 26(a), the molten and solidified material of the elastic film is not seen between fiber molten and solidified materials 20*m* of the first sheet layer 20A or the second sheet layer 20B.

When the first sheet layer 20A and the second sheet layer 20B are bonded using the molten and solidified material 20*m* of the most part or the part of at least one of the first sheet layer 20A and the second sheet layer 20B as an adhesive as in the first adhesive mode or the third adhesive mode, it is preferable that a part of the first sheet layer 20A and the second sheet layer 20B is not melted since the sheet joined portions 40 are not hardened.

Incidentally, when the first sheet layer 20A and the second sheet layer 20B are nonwoven fabrics, a case in which a part of the first sheet layer 20A and the second sheet layer 20B does not melt includes a mode in which cores (including a central part of a single component fiber in addition to a core in a composite fiber) are left for all fibers of the sheet joined portions 40 while a surrounding part thereof (including a part of a surface layer side of the single component fiber in addition to a sheath in the composite fiber) melts, and a mode in which even though some fibers do not melt at all, remaining fibers all melt or even though cores are left, a surrounding part thereof melts.

When the first sheet layer 20A and the second sheet layer 20B are bonded using the molten and solidified material 30*m* of the elastic film 30 as an adhesive as in the second welding mode and the third welding mode, peel strength becomes high. In the second welding mode, under the condition that a melting point of at least one of the first sheet layer 20A and the second sheet layer 20B is higher than a melting point of the elastic film 30 and a heating temperature at the time of forming the sheet joined portions 40, the elastic film 30 is interposed between the first sheet layer 20A and the second sheet layer 20B, a site corresponding to the sheet joined portions 40 is pressurized and heated, and only the elastic film 30 is melted. In this way, manufacturing can be performed.

Meanwhile, in the third welding mode, under the condition that a melting point of at least one of the first sheet layer 20A and the second sheet layer 20B is higher than a melting point of the elastic film 30, the elastic film 30 is interposed between the first sheet layer 20A and the second sheet layer 20B, a site corresponding to the sheet joined portions 40 is pressurized and heated, and at least one of the first sheet layer 20A and the second sheet layer 20B and the elastic film 30 are melted. In this way, manufacturing can be performed.

From such a viewpoint, the melting point of the elastic film 30 is preferably about 80 to 145° C., the melting point of the first sheet layer 20A and the second sheet layer 20B is preferably about 85 to 190° C., particularly 150 to 190° C., and a difference between the melting point of the first sheet layer 20A and the second sheet layer 20B and the melting point of the elastic film 30 is preferably about 60 to 90° C. In addition, the heating temperature is preferably set to about 100 to 150° C.

In the second welding mode and the third welding mode, when the first sheet layer 20A and the second sheet layer 20B are nonwoven fabrics, the molten and solidified material 30*m* of the elastic film 30 may penetrate between fibers over the entire first sheet layer 20A and second sheet layer 20B in the thickness direction in the sheet joined portions 40 as illustrated in FIG. 25(*c*). However, in a mode in which the molten and solidified material 30*m* penetrates between the fibers to the middle in the thickness direction as illustrated in FIG. 25(*a*), or a mode in which the molten and solidified material 30*m* hardly penetrates between the fibers of the first sheet layer 20A and the second sheet layer 20B as illustrated in FIG. 25(*b*), flexibility of the sheet joined portions 40 becomes high.

FIG. 27 illustrates an example of an ultrasonic sealing device suitable for forming the second welding mode and the third welding mode. In this ultrasonic sealing device, when the sheet joined portions 40 are formed, the first sheet layer 20A, the elastic film 30, and the second sheet layer 20B are fed between an anvil roll 60 having projections 60*a* formed in the pattern of the sheet joined portions 40 on an outer surface and an ultrasonic horn 61. At this time, for example, by setting a feeding speed of the upstream elastic film 30 by a feed drive roll 63 and a nip roll 62 to be lower than a feeding speed on the downstream side of the anvil roll 60 and the ultrasonic horn 61, the elastic film 30 is stretched to a predetermined stretch rate in an MD (machine direction, flow direction) through a path from a nip position by the feed drive roll 63 and the nip roll 62 to a seal position by the anvil roll 60 and the ultrasonic horn 61. The stretch rate of the elastic film 30 can be set by selecting a speed difference between the anvil roll 60 and the feed drive roll 63, and can be set to about 300% to 500%, for example. Reference character 62 indicates the nip roll.

The first sheet layer 20A, the elastic film 30, and the second sheet layer 20B fed between the anvil roll 60 and the ultrasonic horn 61 are heated by ultrasonic vibration energy of the ultrasonic horn 61 while being pressurized between the projections 60*a* and the ultrasonic horn 61 in a state of being stacked in this order. By melting only the elastic film 30 or melting at least one of the first sheet layer 20A and the second sheet layer 20B and the elastic film 30, the joint holes 31 are formed in the elastic film 30. At the same time, the first sheet layer 20A and the second sheet layer 20B are bonded through the joint holes 31. Therefore, in this case, by selecting a size, a shape, a separation interval, and an arrangement pattern in a roll length direction and a roll circumferential direction of the projections 60*a* of the anvil roll 60, it is possible to select an area ratio of the sheet joined portions 40.

A reason why the joint holes 31 are formed may not be clear. However, it is considered that the holes are formed when portions corresponding to the projections 60*a* of the anvil roll 60 in the elastic film 30 are melted and detached from the surroundings. In this instance, a portion between adjacent joint holes 31 aligned in the stretchable direction ED in the elastic film 30 is cut from portions on both sides in the stretchable direction by the joint holes 31 as illustrated in FIG. 9(*a*) and FIG. 11(*a*), and loses support on both sides in a contracting direction. Thus, in a range in which continuity in a direction orthogonal to the contracting direction can be maintained, a center side in the direction LD orthogonal to the stretchable direction ED more contracts until the center side is balanced with a center side in the stretchable direction, and the joint holes 31 enlarge in the stretchable direction ED.

A constituent material of the first sheet layer 20A and the second sheet layer 20B can be used without particular limitation as long as the constituent material is a sheet-like material. However, it is preferable to use a nonwoven fabric from a viewpoint of air permeability and flexibility. A row material of the nonwoven fabric is not particularly limited. For example, examples thereof may include a polyolefin-based synthetic fiber such as polyethylene or polypropylene, a polyester-based synthetic fiber, a polyamide-based synthetic fiber, etc., a regenerated fiber such as rayon or cupra, a natural fiber such as cotton, or a mixed fiber, a composite fiber, etc. in which two or more of these materials are used. Further, the nonwoven fabric may be manufactured by any processing.

Examples of a processing method may include a known method, for example, a spunlace method, a spunbond method, a thermal bond method, a meltblown method, a needle punch method, an air through method, a point bond method, etc. In the case of using a nonwoven fabric, a basis weight is preferably set to about 10 to 25 g/m². Further, a part or all of the first sheet layer 20A and the second sheet layer 20B may correspond to a pair of layers faced to each other by folding a single material. For example, as in the illustrated embodiment, in the waist end portions 23, a constituent material located on the outside may be used as the second sheet layer 20B, a folded portion 20C folded back to an internal surface side at a waist opening edge thereof may be used as the first sheet layer 20A, and the elastic film 30 may be interposed therebetween. Further, in other portions, a constituent material located on the inside may be used as the first sheet layer 20A, a constituent material located on the outside may be used as the second sheet layer 20B, and the elastic film 30 may be interposed therebetween. Naturally, the constituent material of the first sheet layer 20A and the constituent material of the second sheet layer 20B may be individually provided over the entire region in the front-back direction LD, and the elastic film 30 may be interposed between the constituent material of the first sheet layer 20A and the constituent material of the second sheet layer 20B without folding back the constituent materials.

The elastic film 30 is not particularly limited. As long as the elastic film 30 is a thermoplastic resin film having elasticity, in addition to a non-perforated film, it is possible to use a film in which a plurality of holes or slits is formed for ventilation. In particular, it is preferable that the elastic film 30 has a tensile strength in the width direction WD (stretchable direction ED, MD) of 8 to 25 N/35 mm, a tensile strength in the front-back direction LD (direction LD orthogonal to the stretchable direction, CD (cross direction)) of 5 to 20 N/35 mm, a tensile elongation in the width direction WD of 450 to 1,050%, and a tensile elongation in the front-back direction LD of 450 to 1,400%. A thickness of the elastic film 30 is not particularly limited. However, the thickness is preferably about 20 to 40 μm.

(Stretchable Region)

A region having the elastic sheet stretchable structure 20X in the outer member 20 has a stretchable region that can be stretched and contracted in the width direction WD. In a stretchable region 80, the elastic film 30 has a portion 32 (see FIG. 12) that is linearly continuous along the width direction WD, which is contracted in the width direction WD by the contraction force of the elastic film 30 and is extensible in the width direction WD. More specifically, in a state where the elastic film 30 is stretched in the width direction WD, the first sheet layer 20A and the second sheet layer 20B are bonded through the joint holes 31 of the elastic film 30 at intervals in each of the width direction WD and the front-back direction LD orthogonal thereto (the direction LD orthogonal to the stretchable direction) to form a plurality of sheet joined portions 40, thereby forming the elastic sheet stretchable structure 20X. Further, in the stretchable region 80, the joint holes 31 are disposed so that the elastic film 30 has the portion 32 that is linearly continuous along the width direction WD, thereby imparting such elasticity.

In the stretchable region, the first sheet layer 20A and the second sheet layer 20B between the sheet joined portions 40 swell in a direction in which they are separated from each other, thereby forming contraction wrinkles 25f and 25F extending in the front-back direction LD in the natural length state as illustrated in FIG. 9 and FIG. 12(*b*). Further, in a worn state of being stretched to some extent in the width direction WD, the contraction wrinkles 25F are left even though the contraction wrinkles 25F are extended. In addition, as in the illustrated embodiment, when the first sheet layer 20A and the second sheet layer 20B are not bonded to the elastic film 30 at least in a portion other than between the first sheet layer 20A and the second sheet layer 20B in the sheet joined portions 40, gaps are formed between the joint holes 31 and the sheet joined portions 40 in the elastic film 30, as can be seen from FIG. 9(*c*) assuming a worn state and FIG. 9(*a*) assuming an unfolded state of the first sheet layer 20A and the second sheet layer 20B, in these states. Even when the material of the elastic film 30 is a non-porous film or sheet, air permeability is imparted by the gaps. Further, in the natural length state, the joint holes 31 are squeezed due to further contraction of the elastic film 30, and a gap is hardly formed between the joint holes 31 and the sheet joined portions 40.

It is desirable that an elongation at elastic limit of the stretchable region 80 in the width direction WD is 200% or more (preferably 265 to 295%). The elongation at elastic limit of the stretchable region 80 is substantially determined by the stretch rate of the elastic film 30 at the time of manufacture, and the elastic limit elongation decreases due to factors that inhibit contraction in the width direction WD based thereon. A main factor of such inhibition is a ratio of the length L of the sheet joined portions 40 per unit length in the width direction WD, and the elongation at elastic limit decreases as this ratio increases. In a normal case, since the length L of the sheet joined portions 40 has a correlation with an area ratio of the sheet joined portions 40, the elongation at elastic limit of the stretchable region 80 can be adjusted by the area ratio of the sheet joined portions 40.

The stretching stress of the stretchable region 80 can be mainly adjusted by a sum of an orthogonal direction LD distance (separation distance d) of the portion 32 (FIG. 12(*a*)) in which the elastic film 30 linearly continues along the width direction WD.

The area ratio of the sheet joined portions 40 and the area of each of the sheet joined portions 40 in the stretchable region 80 can be determined as appropriate and are preferably within the following ranges in a normal case.

Area of each of sheet joined portions 40: 0.14 to 3.5 mm² (particularly 0.14 to 1.0 mm²)

Area ratio of sheet joined portions 40: 1.8 to 19.1% (particularly 1.8 to 10.6%)

As described above, the elongation at elastic limit and stretching stress of the stretchable region 80 can be adjusted by the area of the sheet joined portions 40. Thus, as illustrated in FIG. 7, a plurality of regions having different area ratios of the sheet joined portions 40 may be provided in the stretchable region 80 to change fitting according to the site. In the embodiment illustrated in FIG. 7, regions 81 obliquely extending along roots of legs and edge portion regions 82 of leg openings in the front body F correspond to a flexibly stretching and contracting region in which the area ratio of the sheet joined portions 40 is high comparing to other regions, and thus the stretching stress is weak. In addition, ileum facing regions 83 and edge portion regions 82 of leg openings in the back body B also correspond to a flexibly stretching and contracting region in which the area ratio of the sheet joined portions 40 is high comparing to other regions, and thus the stretching stress is weak.

(Non-Stretchable Region)

In a region having the elastic sheet stretchable structure 20X in the outer member 20, as illustrated in FIG. 7, a non-stretchable region 70 may be provided at least on one side of the stretchable region 80 in the width direction. Arrangement of the stretchable region 80 and the non-stretchable region 70 can be determined as appropriate. In the case of the outer member 20 of the underpants-type disposable diaper as in the present embodiment, a portion overlapping the absorbent body 13 is a region not requiring stretching and contraction. Thus, as in the illustrated embodiment, it is preferable to form a part or all of the portion overlapping the absorbent body 13 (it is desirable to include almost the entire inner/outer fixing region 10B) into the non-stretchable region 70. Naturally, the non-stretchable region 70 may be provided from a region overlapping the absorbent body 13 to a region not overlapping the absorbent body 13 away from the region in the width direction WD or the front-back direction LD, and the non-stretchable region 70 may be provided only in the region not overlapping the absorbent body 13.

The non-stretchable region 70 is a region not having the portion that linearly continues along the width direction WD due to the presence of the joint holes 31 even though the elastic film 30 is continuous in the width direction WD. Therefore, even though in a state where the elastic film 30 is stretched in the width direction WD, the first sheet layer 20A and the second sheet layer 20B are bonded through the joint holes 31 of the elastic film 30 at intervals in each of the width direction WD and the front-back direction LD orthogonal thereto, and a plurality of sheet joined portions 40 is formed, thereby forming the entire elastic sheet stretchable structure 20X including both the stretchable region 80 and the non-stretchable region 70, the elastic film 30 is not linearly continuous along the width direction WD in the non-stretchable region 70. Thus, the contraction force of the elastic film 30 hardly acts on the first sheet layer 20A and the second sheet layer 20B, the elasticity is almost lost, and the elongation at elastic limit is close to 100%.

In such a non-stretchable region 70, the first sheet layer 20A and the second sheet layer 20B are bonded by a plurality of sheet joined portions 40 arranged at intervals, and the sheet joined portions 40 are not continuous. Thus, a decrease in flexibility is prevented.

An arrangement pattern of the joint holes 31 in the elastic film 30 in the non-stretchable region 70 can be determined as appropriate.

The area ratio of the sheet joined portions 40 and the area of each of the sheet joined portions 40 in the non-stretchable region can be determined as appropriate. However, in a normal case, the area ratio and the area are preferably within the following ranges since the non-stretchable region 70 does not become hard due to the small area of each of the sheet joined portions 40 and the low area ratio of the sheet joined portions 40.

Area of each of sheet joined portions 40: 0.10 to 0.75 mm$^2$ (particularly 0.10 to 0.35 mm$^2$)

Area ratio of sheet joined portions 40: 4 to 13% (particularly 5 to 10%)

In the above example, the elastic film is used as the elastic sheet. However, an elastic nonwoven fabric may be used. Further, an elastic nonwoven fabric may be provided on one side or both sides of the elastic film, which may be interposed between the first sheet layer 20A and the second sheet layer 20B.

<Description of Terms in Specification>

The following terms in the specification have the following meanings unless otherwise specified in the specification.

The "front body" and the "back body" refer to portions on the front side and the back side, respectively, with respect to a center of the underpants-type disposable diaper in the front-back direction as a boundary. In addition, the crotch portion refers to a range in the front-back direction including the center of the underpants-type disposable diaper in the front-back direction, and refers to a range of a portion having a narrowing portion in the front-back direction when the absorbent body has the narrowing portion.

The "elongation at elastic limit" refers to an elongation of an elastic limit (in other words, a state in which the first sheet layer and the second sheet layer are fully unfolded) in the stretchable direction ED, and represents a length at the time of the elastic limit as a percentage when the natural length is 100%.

The "area ratio" refers to a ratio of a target portion to a unit area, and is represented as a percentage of a value obtained by dividing a total area of target portions (for example, the sheet joined portions 40, the openings of the joint holes 31, and the vent holes) in target regions (for example, the stretchable region 80 and the non-stretchable region 70) by an area of the target regions. In particular, the "area ratio" in a region having the stretchable structure refers to an area ratio in a state of being stretched to the elastic limit in the stretchable direction ED. In a mode in which a plurality of target portions is provided at intervals, it is desirable to obtain the area ratio by setting a size of the target regions to include ten or more target portions.

The "stretch rate" refers to a value when the natural length is 100%.

The "basis weight" is measured as below. A sample or a test piece is pre-dried, and then is left in a test room or a device in a standard state (temperature 23±1° C., relative humidity 50±2% in a test location), and is put in a constant weight state. Pre-drying refers to setting the weight of the sample or the test piece to a constant weight in an environment in which temperature is 100° C. Incidentally, pre-drying is unnecessary for a fiber having an official moisture regain of 0.0%. A sample having dimensions of 100 mm×100 mm is cut off from the test piece in the constant weight state using a sampling template (100 mm×100 mm). A weight of the sample is measured and multiplied by 100 to calculate a weight per square meter, and the weight is set to the basis weight.

The "thickness" of the absorbent body is measured using a thickness measuring instrument of Ozaki Mfg. Co., Ltd. (Peacock, Dial Thickness Gauge Large Type, Model J-B (measurement range 0 to 35 mm) or Model K-4 (measurement range 0 to 50 mm)) by horizontally placing the sample and the thickness measuring device.

A "thickness" other than the above thickness is automatically measured under the condition of load: 0.098 N/cm$^2$ and pressure area: 2 cm$^2$ using an automatic thickness meter (KES-G5 handy compression measurement program).

The "tensile strength" and the "tensile elongation (breaking elongation) refer to values measured by setting an initial chuck interval (distance between marked lines) to 50 mm and a tensile speed to 300 mm/min in accordance with JIS K7127: 1999 "Plastics-Determination of tensile properties-" except that the test piece has a rectangular shape of width 35 mm×length 80 mm. As a tensile testing machine, for example, AUTOGRAPH AGS-G100N manufactured by SHIMADZU CORPORATION can be used.

The "stretching stress" refers to the tensile stress (N/35 mm) measured when stretching in the elastic region by a tensile test setting an initial chuck interval (distance between marked lines) to 50 mm and a tensile speed to 300 mm/min in accordance with JIS K7127: 1999 "Plastics-Determination of tensile properties-", and a degree of stretching can be appropriately determined depending on the test object. It is preferable that the test piece has a rectangular shape having a width of 35 mm and a length of 80 mm or more. However, when a test piece having a width of 35 mm may not be cut out, the test piece is created to have a width allowing cutting out, and a measured value is set to a value converted to have the width of 35 mm. In addition, even in a case in which the target region is small and sufficient test pieces may not be collected, when the magnitude of stretching stress is compared, even a suitably small test piece can be compared at least as long as test pieces of the same size are used. As a tensile testing machine, for example, AUTOGRAPH AGS-G100N manufactured by SHIMADZU CORPORATION can be used.

The "unfolded state" refers to a flatly unfolded state without contraction or slack.

Dimensions of each portion refer to dimensions in an unfolded state rather than the natural length state unless otherwise stated.

When there is no description about an environmental condition in a test or measurement, it is presumed that the test or measurement is performed in a test room or a device in a standard state (temperature 23±1° C., relative humidity 50±2% in a test location).

INDUSTRIAL APPLICABILITY

As long as a stretchable region to which an elastic sheet stretchable structure can be applied is included, the invention can be used for disposable wearing articles in general such as various disposable diapers of a tape type, a pad type, etc., a sanitary napkin, a disposable wearing article for swimming or playing in the water, etc. in addition to the underpants-type disposable diaper as in the above example.

REFERENCE SIGNS LIST

10 Inner member
10B Inner/outer fixing region
11 Top sheet
12 Liquid impervious sheet
13 Absorbent body
13N Narrower portion
14 Package sheet
17 Non-absorbent body side portion
20 Outer member
20A First sheet layer
20B Second sheet layer
20C Folded portion
20X Elastic sheet stretchable structure
21 Side seal portion
23 Waist end portion
24 Waist portion elastic member
25F, 25f Contraction wrinkles
29 Around-leg line
30 Elastic film
31 Joint hole
33 Vent hole
40 Sheet joined portion (first joined portion)
41 Second joined portion
42 Third joined portion
43 Fourth joined portion
70 Non-stretchable region
80 Stretchable region
90 Three-dimensional gather
93 Fallen portion
94 Free portion
95 Gather sheet
96 Gather elastic member
B Back body
ED Stretchable direction (width direction)
F Front body
L Intermediate portion
LD Orthogonal direction (front-back direction)
T Lower torso portion
sf Small pleat
bf Large pleat

The invention claimed is:

1. An elastic member having an elastic sheet stretchable structure in which an elastic sheet is interposed between a first sheet layer having air permeability and a second sheet layer having air permeability, and the first sheet layer and the second sheet layer are bonded through joint holes penetrating the elastic sheet or via the elastic sheet at a plurality of sheet joined portions arranged at intervals, wherein a stretchable region exhibiting the elastic sheet stretchable structure is allowed to be stretched and contracted in a stretchable direction by a contraction force of the elastic sheet, the joined portions have first joined portions and second joined portions, a first joined portion row is formed such that the first joined portions are spaced along an alignment direction in which alignment is performed at an angle intersecting the stretchable direction in a range of 45 degrees to 135 degrees, the first joined portions in the first joined portion row are formed to have a length of 0.3 to 7.0 mm with respect to an orthogonal direction orthogonal to the stretchable direction, the first joined portion row is formed to have a formation pitch of 2.0 to 20.0 mm with respect to the stretchable direction, as a distance with respect to the orthogonal direction determined by a mutual relationship between the adjacent first joined portions in the first joined portion row, a ratio of (a separation distance between adjacent first joined portions)/(a distance from one point of a joined portion to one corresponding point of an adjacent first joined portion) is 5 to 60% in percentage, a plurality of the first joined portion rows is formed at intervals in the stretchable direction, and a plurality of the second joined portions having a shorter length than a length of the first joined portions is formed in the alignment direction between the first joined portion rows.

2. The elastic member according to claim 1, wherein a plurality of second joined portion rows in which the second joined portions are spaced in the alignment direction is formed between the first joined portion rows.

3. The elastic member according to claim 2, wherein a joined portion having the length of the first joined portions or a longer length is not formed in the second joined portion rows.

4. An underpants-type disposable wearing article comprising:
- an integrated outer member covering from a front body to a back body or outer members separately provided for the front body and the back body;
- an inner member attached to an intermediate portion of the outer member in a width direction to extend to both front and back sides of a crotch portion;
- side seal portions in which both side portions of the outer member in the front body and both side portions of the outer member in the back body are bonded to each other; and
- a waist opening and a pair of right and left leg openings,
- the outer member including an elastic member having an elastic sheet stretchable structure in which an elastic sheet is interposed between a first sheet layer having air permeability and a second sheet layer having air permeability, and the first sheet layer and the second sheet layer are bonded through joint holes penetrating the elastic sheet or via the elastic sheet at a plurality of sheet joined portions arranged at intervals,
- wherein a stretchable region exhibiting the elastic sheet stretchable structure is allowed to be stretched and contracted in a stretchable direction by a contraction force of the elastic sheet,
- the joined portions have first joined portions and second joined portions,
- a first joined portion row is formed such that the first joined portions are spaced along an alignment direction in which alignment is performed at an angle intersecting the stretchable direction in a range of 45 degrees to 135 degrees,
- the first joined portions in the first joined portion row are formed to have a length of 0.3 to 7.0 mm with respect to an orthogonal direction orthogonal to the stretchable direction,
- the first joined portion row is formed to have a formation pitch of 2.0 to 20.0 mm with respect to the stretchable direction,
- as a distance with respect to the orthogonal direction determined by a mutual relationship between the adjacent first joined portions in the first joined portion row,
- a ratio of (a separation distance between adjacent first joined portions)/(a distance from one point of a joined portion to one corresponding point of an adjacent first joined portion) is 5 to 60% in percentage,
- a plurality of the first joined portion rows is formed at intervals in the stretchable direction, and
- a plurality of the second joined portions having a shorter length than a length of the first joined portions is formed in the alignment direction between the first joined portion rows,
- wherein the outer member in at least one of the front body and the back body has the elastic sheet stretchable structure over a range in the width direction corresponding to a space between the side seal portions at least in a partial range in a front-back direction so that an stretchable direction of a stretchable region thereof corresponds to the width direction.

\* \* \* \* \*